(12) United States Patent
Hayashi et al.

(10) Patent No.: US 8,071,123 B2
(45) Date of Patent: Dec. 6, 2011

(54) PROCESS FOR PRODUCING EDIBLE ORALLY ADMINISTERED AGENT OF LAMINATE FILM FORM AND COMPRESSION BONDING APPARATUS

(75) Inventors: Yasuo Hayashi, Izumi-gun (JP); Kazuya Yano, Izumi-gun (JP); Tsutomu Awamura, Izumi-gun (JP); Kazuyoshi Sudeji, Izumi-gun (JP)

(73) Assignee: Kyukyu Pharmaceutical Co., Ltd., Tokyo (JP)

( * ) Notice: Subject to any disclaimer, the term of this patent is extended or adjusted under 35 U.S.C. 154(b) by 1994 days.

(21) Appl. No.: 10/534,423

(22) PCT Filed: Dec. 1, 2003

(86) PCT No.: PCT/JP03/15338
§ 371 (c)(1),
(2), (4) Date: May 10, 2005

(87) PCT Pub. No.: WO2004/050008
PCT Pub. Date: Jun. 17, 2004

(65) Prior Publication Data
US 2006/0062830 A1      Mar. 23, 2006

(30) Foreign Application Priority Data

Dec. 2, 2002 (JP) .................... 2002-349908
Sep. 8, 2003 (JP) .................... 2003-315503

(51) Int. Cl.
*A61K 9/70* (2006.01)
*A61K 9/20* (2006.01)
*A61J 3/00* (2006.01)
*B29C 65/00* (2006.01)
*B29C 43/30* (2006.01)

(52) U.S. Cl. ........ 424/443; 156/437; 156/443; 156/459; 264/171.1; 424/441; 425/505

(58) Field of Classification Search .................. None
See application file for complete search history.

(56) References Cited

U.S. PATENT DOCUMENTS 6,818,087 B1 * 11/2004 Roreger et al. ............ 156/145
2004/0137040 A1 * 7/2004 Nogami .................... 424/443

FOREIGN PATENT DOCUMENTS
JP          64-27897          1/1989
(Continued)

*Primary Examiner* — Ernst Arnold
*Assistant Examiner* — Christopher R Lea
(74) *Attorney, Agent, or Firm* — Wenderoth, Lind & Ponack, L.L.P.

(57) ABSTRACT

Two resin films each provided with an orally administrable edible agent layer are joined so that administrable agent layers face each other, drawn into a nip between a pair of press rolls, pressurized at back surfaces to bond the administrable agent layers together, and conveyed in a direction substantially conforming to a tangential direction at a pressurization zone of the press rolls. A delamination roll disposed in the conveying direction is used to draw only one of the two resin films sandwiching the bonded plural administrable agent layers in a direction different from the conveying direction, while continuously conveying the other resin film retaining the plural administrable agent layers in the conveying direction. This allows only one of the joined two resin films to be delaminated. The obtained pressure bonded product, that is, an orally administrable edible agent of laminate film form can be punched out into predetermined shapes.

38 Claims, 15 Drawing Sheets

FOREIGN PATENT DOCUMENTS

| | | |
|---|---|---|
| JP | 2559301 | 9/1996 |
| JP | 3041977 | 7/1997 |
| JP | 9-235220 | 9/1997 |
| JP | 2001-504106 | 3/2001 |
| JP | 2001-130142 | 5/2001 |
| JP | 2001-506640 | 5/2001 |
| JP | 2001-176751 | 6/2001 |
| JP | 2001-288074 | 10/2001 |
| JP | 2001-341397 | 12/2001 |
| JP | 2002-191343 | 7/2002 |
| JP | 2002-234070 | 8/2002 |

* cited by examiner

Technique of the invention

Lamination coating technique

PROCESS FOR PRODUCING EDIBLE ORALLY ADMINISTERED AGENT OF LAMINATE FILM FORM AND COMPRESSION BONDING APPARATUS

TECHNICAL FIELD

The present invention relates to a novel and improved method for producing an orally administrable edible agent of laminate film form having a multilayer structure including laminated extremely thin layers of orally administrable edible substances of drugs, quasi drugs, cosmetics and food, and a pressure bonding apparatus of the orally administrable edible agent of laminate
film form for use in this producing method.

More specifically, the present invention relates to a novel and improved method for producing an orally administrable edible agent of laminate film form having a multilayer structure including laminated extremely thin layers with high productivity, the orally administrable agent consisting of substances accepted as food and food additives and/or drugs and pharmaceutical additives approved for oral administration, for example, oral transmucosal patches applied to upper jaw or gingival mucosa or nasal mucosa, oral disease preventive patches applied to an affected area in oral cavity for treatment and protection, oral treatment patches, bad breath preventive patches, bad breath stop patches, pharmaceutical preparations for oral administration dissolved in oral cavity and absorbed mainly in alimentary canal, quasi drugs having a deodorizing effect or a therapeutic effect, food, etc., and further relates to a pressure bonding apparatus of the orally administrable edible agent of laminate film form for use in this producing method.

BACKGROUND ART

Various techniques for forming orally administrable edible agents such as drugs, quasi drugs, cosmetics, food, etc. into a shape of a sheet or a film have been proposed. The term "film form" is used herein for generally referring to a shape of a thin layer such as a film or a sheet.

For example, Japanese Patent No. 2559301 discloses production of an orally administrable agent of sheet form by spreading an orally administrable agent preparation solution containing a mixture of a film forming agent, a gel forming agent, an active substance, an inert filler, and a polar solvent on siliconized paper using a coating device, and drying the solution at 80° C. for 10 to 15 minutes, but does not disclose a structure including laminated multiple orally administrable agent layers.

Japanese Patent Laid-Open No. 2001-504106 describes production of an orally administrable agent of film form by coating an orally administrable agent preparation solution on an appropriate carrier material, drying the solution, and then delaminating, or peeling, the obtained orally administrable agent of film form from the carrier material. The carrier material includes a non-siliconized polyethylene terephthalate film, non-siliconized kraft paper, polyethylene-impregnated kraft paper, or a non-silicone polyethylene film, and a knife over roll coating head is preferably used as a coating technique. This document, however, does not teach production of a film orally administrable agent of film form having a structure including laminated multiple orally administrable agent layers.

WO98/56266 and Japanese Patent Laid-Open No. 2002-191343 disclose a method for producing food having a multilayer structure by feeding edible materials of different types and/or blend-ratio into hopper-chambers respectively which are partitioned off a hopper by partition plates, forming a plurality of primary rolled sheets of strip form by a primary common mill roll below the hopper-chambers, superposing the sheets one on another with a certain space therebetween in a direction perpendicular to a longitudinal direction of the sheets during conveyance, and rolling the superposed sheets by a secondary mill roll to bond them to each other. This method is, however, adapted to form a thick multilayer sheet such as cookie dough, pie dough or cracker dough having plasticity by rolling, and cannot produce orally administrable edible agents such as drugs, food, etc. formed by pressure bonding edible materials having a plurality of extremely thin layers of several hundreds µm to several tens thick into a thin multilayer structure having an entire thickness of several thousands µm to several tens µm.

The following is a patent document that relates to obtaining an edible multilayer structure of film form of several thousands µm to several tens µm thick.

For example, Japanese Patent Laid-Open No. 2001-506640 discloses an orally administrable agent of sheet or tape form for administering buprenorphine to oral mucosa, and a producing method for combining a plurality of materials of sheet or tape form coated with an orally administrable agent preparation solution containing buprenorphine so as to form a multilayer material, but does not teach at all a specific method for producing a multilayer structure and a specific producing apparatus for obtaining the multilayer structure.

Further, in the above-described Japanese Patent Laid-open No. 2001-506640, a tape, a sheet, or a foil coated with the orally administrable agent preparation solution and dried is separated as it is by cutting or punching out into a dose or a plurality of doses, and thus delaminating the tape, the sheet, or the foil from the cut piece for administration into the oral cavity is troublesome. When used without the material being delaminated such as the tape, the sheet, or the foil that provides uncomfortable feeling in the oral cavity, the use thereof is restricted and the use is further limited to an inedible material.

Japanese Patent Laid-Open No. 9-235220 discloses an orally administrable agent of film form having a multilayer structure including a drug-containing layer, a non-adhesive layer and an adhesive layer. A producing method thereof disclosed in an embodiment includes repeatedly spreading or spraying an orally administrable agent layer preparation solution on a petri dish made of polytetrafluoroethylene (Teflon®) and delaminating the spread or sprayed orally administrable agent layer preparation solution from the petri dish after drying to obtain an orally administrable agent of film form having a desired multilayer structure. Such a producing method cannot be industrially used, though used in a laboratory. Further, if another orally administrable agent layer preparation solution is manually spread or sprayed on the formed orally administrable agent layer to form a multilayer structure, it is difficult to spread or spray an accurate amount of preparation solution to prevent control of an accurate amount of drug ingredient, and the obtained multilayer orally administrable agent of film form cannot satisfy quantitative accuracy required for pharmaceutical preparations. This document does not teach a producing apparatus at all.

Japanese Patent Laid-Open No. 2001-288074 filed by the applicant of this application proposes a troche (an orally administrable edible agent) of film form including three layers of a covering layer (a), a drug layer I (b), and a drug layer II (c) laminated in order of a-b-c-b-a. This document discloses a method for producing the troche of film form including repeatedly coating and drying each orally administrable edible agent layer preparation solution on a polyester delamination film to form a desired multilayer laminated structure.

In producing the orally administrable edible agent of film form having the multilayer laminated structure described in Japanese Patent Laid-Open No. 2001-288074 filed by the applicant of this application, the applicant uses a coating apparatus 200 for continuously coating and drying the orally administrable edible agent layer preparation solution on a continuously moving resin film as shown in FIG. 1. The coating apparatus 200 guides a resin film 202 set on a resin film unwinding shaft 201 into a drying oven 205 through a nip between a guide roll 203 and a doctor roll 204, and winds up the resin film 202 on a resin film winding shaft 206, thereby continuously moving the resin film 202. In the meantime, an orally administrable edible agent layer preparation solution 208 contained in a dam portion 207 for supplying the orally administrable edible agent layer preparation solution is coated on the resin film, and at this time, a clearance between the resin film 202 on the guide roll 203 and the doctor roll 204 is adjusted to a predetermined dimension to obtain a predetermined coating amount (see the partial enlarged view). A coating layer 208a on the resin film 202 thus formed passes through the drying oven 205 and is dried by hot air uniformly blown from a hot air blowing device 209, and a resin film 210 provided with an orally administrable edible agent layer is wound up on the winding shaft 206 into a roll.

Then, the orally administrable agent layer-formed resin film 210 wound up on the winding shaft 206 into the roll is mounted to the unwinding roll 201 again, the orally administrable edible agent layer preparation solution 208 of the same or different composition is supplied to the dam portion 207 for coating and drying again, and the resin film is wound up on the winding roll 206, thereby producing a resin film including laminated two orally administrable edible agent layers. Repeating such coating and drying steps allows the orally administrable edible agent of film form having a desired multilayer structure to be produced with higher productivity than the conventional methods described above.

However, it has been found that even with the coating method as shown in FIG. 1, accurate control of a coating amount of the orally administrable edible agent layer preparation solution 208 is difficult in producing the orally administrable edible agent of film form having the multilayer structure by repeating the coating and drying steps, and quantitative accuracy required for pharmaceutical preparations cannot be satisfied, like the conventional methods described above.

Specifically, in a first coating step including drying step, the clearance between the doctor roll 204 and the resin film 202 can be set to the predetermined dimension to accurately control the coating amount at a predetermined value. However, a thickness of a dried orally administrable edible agent layer formed in a drying step after the first spreading step varies depending on minor variation of condition of the drying step and environmental conditions such as daily temperature and humidity. Therefore, in a second coating step including drying step, even if the clearance dimension between the doctor roll 204 and the resin film 202 is accurately set, a coating thickness of the second orally administrable edible agent layer further varies depending on variation of the coating thickness of the first orally administrable edible agent layer, since a coating thickness of the orally administrable edible agent layer preparation solution 208 is determined by a clearance between an upper surface of the first dried orally administrable edible agent layer and the doctor roll 204. It is significantly difficult to measure the variation of the thickness of the first edible orally administrable layer 208a after the drying step.

Such an inaccurate coating amount of the orally administrable edible agent layer preparation solution tends to increase as the number of coating steps increases. Further, as the number of coating steps increases, drying time increases. More specifically, drying time for the second orally administrable edible agent layer is 1.5 times longer than that for the first layer, and drying time for a third layer is twice longer than that for the first layer.

In such a situation, in order to obtain an orally administrable edible agent of film form having a multilayer structure including laminated plural thin layers, the applicant attempts to coat and dry an orally administrable edible agent layer preparation solution on a surface of a resin film to produce a resin film provided with an orally administrable edible agent layer having a predetermined thickness, join the resin films together so that orally administrable edible agent layers thereof face each other, pressurize the resin films at back surfaces to pressure bond the orally administrable edible agent layers, and delaminate one of the two resin films sandwiching the bonded orally administrable edible agents.

Then, the orally administrable edible agent having the multilayer structure including laminated plural layers has strength sufficient to form a self-supporting film, and thus the orally administrable edible agent layers adhere to the delaminated resin film to sometimes prevent the orally administrable edible agent layers from being retained on the other intended resin film.

Further, in order to prepare the orally administrable edible agent of film form having the multilayer structure including the laminated plural layers into a predetermined shape, it is efficient that a repeating step of coating, drying and pressure bonding when forming the multiple orally administrable edible agent layers on the surface of the resin film is performed using as wide a resin film as possible, and the resin film is cut into predetermined narrow strips to supply the strips to a preparation step where the strips are punched out into predetermined shapes. However, wildly cutting the wide resin film retaining the orally administrable edible agent layers on the surface thereof into narrow strips may cause distortion, wrinkles or cracks in the orally administrable edible agent layers retained on the resin film.

SUMMARY OF THE INVENTION

The invention is achieved in view of the above described problems, and a first object of the invention is to provide a novel and improved method for producing an orally administrable edible agent of laminate film form having a multilayer structure including laminated extremely thin layers with high productivity that can satisfy quantitative accuracy required for pharmaceutical preparations, and prevents time constraint in a drying step or the like.

A second object of the invention is to provide a method for producing an orally administrable edible agent of laminate film form and a pressure bonding apparatus that can delaminate one of two resin films sandwiching pressure bonded orally administrable edible agent layers, and ensure retaining the orally administrable edible agent layers on the other (another) intended resin film, in pressure bonding a plurality of extremely thin layers of several hundreds µm to several tens µm thick into a thin multilayer structure having an entire thickness of several thousands µm to several tens µm.

A third object of the invention is to provide a pressure bonding apparatus of an orally administrable edible agent of film form with high productivity and operability that prevents distortion, wrinkles or cracks in orally administrable edible agent layers retained on a resin film when a wide resin film retaining the orally administrable edible agent layers is cut into narrow strips for supply to a preparation step.

A fourth object of the invention is to provide a pressure bonding apparatus of an orally administrable edible agent of film form that is generally compact and has flexibility to laminate and pressure bond a predetermined number of administrable agent layers of many types to obtain an orally administrable edible agent layers having a multilayer structure suitable for various use, in pressure bonding a plurality of layers to produce an orally administrable edible agent layer having a multilayer structure.

Specifically, a method for producing an orally administrable edible agent of laminate film form according to a first aspect of the invention is characterized by comprising: an orally administrable agent layer forming step for forming an orally administrable edible agent layer having a predetermined thickness on a surface of a resin film by coating and drying; an orally administrable agent layer pressure bonding step for joining together two orally administrable agent layer-formed resin films provided with orally administrable edible agent layers of the same ingredient or different ingredients obtained in the orally administrable agent layer forming step so that orally administrable edible agent layer surfaces face each other, and pressurizing the resin films at back surfaces by a pair of press rolls to bond the orally administrable edible agent layers together; and a resin film delaminating step for delaminating only one of the joined two resin films by conveying the two resin films sandwiching the bonded orally administrable edible agent layers in a direction substantially conforming to a tangential direction at a pressurization zone of the pair of press rolls, and drawing only one of the two resin films sandwiching the bonded orally administrable edible agent layers in a direction different from the conveying direction along a peripheral surface of a delamination roll disposed in the conveying direction while continuously conveying the other resin film retaining the orally administrable edible agent layers in the conveying direction.

The orally administrable edible agent of laminate film form has strength sufficient to form a self-supporting film to cause the orally administrable edible agent layers to adhere to one resin film to be delaminated, which tends to cause trouble that the orally administrable edible agent layers cannot be retained on the other intended resin film. According to the first aspect of the invention, the orally administrable edible agent layers can be reliably retained on the other intended resin film by conveying the two resin films sandwiching the bonded orally administrable edible agent layers in the direction substantially conforming to the tangential direction at the pressurization zone of the pair of press rolls, and drawing one of the two resin films sandwiching the bonded orally administrable edible agent layers in the direction different from the conveying direction along the peripheral surface of the delamination roll disposed in the conveying direction while continuously conveying the other resin film retaining the orally administrable edible agent layers in the conveying direction, thereby providing a method for producing an orally administrable edible agent of laminate film form with high productivity.

Particularly, a laminated structure obtained by the method for producing the orally administrable edible agent of laminate film form using the pressure bonding technique according to the invention for bonding the orally administrable edible agent layers together by the pair of press rolls is characterized in that each of the laminated orally administrable edible agent layers is definitely divided. Specifically, in the laminated structure obtained by the method of the invention, as shown in a sectional photomicrograph in FIG. 18, a boundary X between the orally administrable edible agent layers appears clear and each of the laminated orally administrable agent layers can be definitely identified. On the other hand, in a laminated structure obtained by a conventional lamination coating technique of repeating coating and drying steps for lamination, a boundary Y between orally administrable edible agent layers appears unclear and blurred, and each of the laminated orally edible administrable agent layers cannot be definitely identified. Specifically, the laminated structure in which each of the laminated orally administrable edible agent layers is definitely divided is a novel laminated structure first obtained by the orally administrable edible agent of laminate film form produced by the method of the invention.

According to the method for producing the orally administrable edible agent of laminate film form of the invention, a larger desired number of orally administrable edible agent layers may be formed as required. Such a method for producing an orally administrable edible agent of laminate film form is according to a second aspect of the invention, and is characterized by comprising: an orally administrable agent layer forming step for forming an orally administrable edible agent layer having a predetermined thickness on a surface of a resin film by coating and drying; an orally administrable agent layer pressure bonding step for joining together two orally administrable agent layer-formed resin films provided with orally administrable edible agent layers of the same ingredient or different ingredients obtained in the orally administrable agent layer forming step so that orally administrable edible agent layer surfaces face each other, and pressurizing the resin films at back surfaces by a pair of press rolls to bond the orally administrable edible agent layers together; a resin film delaminating step for delaminating only one of the two resin films by conveying the two resin films sandwiching the bonded orally administrable edible agent layers in a direction substantially conforming to a tangential direction at a pressurization zone of the pair of press rolls, and drawing only one of the two resin films sandwiching the bonded orally administrable edible agent layers in a direction different from the conveying direction along a peripheral surface of a delamination roll disposed in the conveying direction while continuously conveying the other resin film retaining the orally administrable edible agent layers in the conveying direction; a multiple orally administrable agent layers pressure bonding step for joining together the resin film retaining the bonded plural orally administrable edible agent layers obtained in the resin film delaminating step and another resin film provided with a single or a plurality of orally administrable edible agent layer/layers of the same or different ingredient as or from the bonded plural orally administrable edible agent layers so that orally administrable edible agent layer surfaces face each other, and pressurizing the resin films at back surfaces by a pair of press rolls to bond the orally administrable edible agent layers together; and a resin film delaminating and removing step for delaminating only one of the two resin films by conveying the two resin films sandwiching the bonded multiple orally administrable edible agent layers in a direction substantially conforming to a tangential direction at a pressurization zone of the pair of press rolls, and drawing only one of the two resin films sandwiching the bonded multiple orally administrable edible agent layers in a direction different from the conveying direction along a peripheral surface of a delamination roll disposed in the conveying direction while continuously conveying the other resin film retaining the multiple orally administrable edible agent layers in the conveying direction.

According to the second aspect of the invention, the orally administrable edible agent of laminate film form including a desired number of orally administrable edible agent layers laminated can be efficiently produced by the pressure bonding technique.

For the above described method for producing the orally administrable edible agent of laminate film form of the invention, the orally administrable agent layer forming step, the orally administrable agent layer pressure bonding step, the resin film delaminating step, and if required, the multiple orally administrable agent layers pressure bonding step and the resin film delaminating and removing step may be carried out in a continuous manner as a series of steps, and also may be carried out in a batch manner by winding the resin film provided with the single or the plurality of orally administrable edible agent layer/layers obtained in an intermediate step into a roll to once form a rolled film, and using the rolled film as a starting material of the following step.

A method for producing an orally administrable edible agent of laminate film form according to a third aspect of the invention carried out in a batch manner by forming a rolled film in an intermediate step is characterized by comprising: an orally administrable agent layer forming step for forming an orally administrable edible agent layer having a predetermined thickness on a surface of a resin film by coating and drying; a rolled film forming step for winding the orally administrable agent layer-formed resin film obtained in the orally administrable agent layer forming step into a roll to form a rolled film; a rolled film orally administrable agent layer pressure bonding step for unwinding and joining together two rolled films provided with orally administrable edible agent layers of the same ingredient or different ingredients obtained in the rolled film forming step so that orally administrable edible agent layer surfaces face each other, and pressurizing the resin films at back surfaces by a pair of press rolls to bond the orally administrable edible agent layers together; and a resin film delaminating step for delaminating only one of the joined two resin films by conveying the two resin films sandwiching the bonded orally administrable edible agent layers in a direction substantially conforming to a tangential direction at a pressurization zone of the pair of press rolls, and drawing only one of the two resin films sandwiching the bonded orally administrable edible agent layers in a direction different from the conveying direction along a peripheral surface of a delamination roll disposed in the conveying direction while continuously conveying the other resin film retaining the orally administrable edible agent layers in the conveying direction.

For the method for producing the orally administrable edible agent of laminate film form of the invention in the batch manner, a larger desired number of orally administrable edible agent layers may be formed if required. This method is according to a fourth aspect of the invention, and is characterized by comprising: an orally administrable agent layer forming step for forming an orally administrable edible agent layer having a predetermined thickness on a surface of a resin film by coating and drying; a rolled film forming step for winding the orally administrable agent layer-formed resin film obtained in the orally administrable agent layer forming step into a roll to form a rolled film; a rolled film orally administrable agent layer pressure bonding step for unwinding and joining together two rolled films provided with orally administrable edible agent layers of the same ingredient or different ingredients obtained in the rolled film forming step so that orally administrable edible agent layer surfaces face each other, and pressurizing the resin films at back surfaces by a pair of press rolls to bond the orally administrable edible agent layers together; a resin film delaminating step for delaminating only one of the joined two resin films by conveying the two resin films sandwiching the bonded orally administrable edible agent layers in a direction substantially conforming to a tangential direction at a pressurization zone of the pair of press rolls, and drawing only one of the two resin films sandwiching the bonded orally administrable edible agent layers in a direction different from the conveying direction along a peripheral surface of a delamination roll disposed in the conveying direction while continuously conveying the other resin film retaining the orally administrable edible agent layers in the conveying direction; a plural orally administrable agent layers-retained rolled film forming step for winding the resin film retaining the bonded plural orally administrable edible agent layers obtained in the resin film delaminating step into a roll to form a rolled film; a rolled film multiple orally administrable agent layers pressure bonding step for unwinding and joining together the plural orally administrable agent layers-retained rolled film retaining the bonded plural orally administrable edible agent layers obtained in the plural orally administrable agent layers-retained rolled film forming step and another rolled film retaining a single or a plurality of orally administrable edible agent layer/layers of the same or different ingredient as or from the bonded plural orally administrable edible agent layers so that orally administrable edible agent layer surfaces face each other, and pressurizing the resin films at back surfaces by a pair of press rolls to bond the orally administrable edible agent layers together; and a resin film delaminating and removing step for delaminating only one of the two resin films by conveying the two resin films sandwiching the bonded multiple orally administrable edible agent layers in a direction substantially conforming to a tangential direction at a pressurization zone of the pair of press rolls, and drawing only one of the two resin films sandwiching the bonded multiple orally administrable edible agent layers in a direction different from the conveying direction along a peripheral surface of a delamination roll disposed in the conveying direction while continuously conveying the other resin film retaining the multiple orally administrable edible agent layers in the conveying direction.

According to the fourth aspect of the invention, the orally administrable edible agent of laminate film form including a desired number of orally administrable edible agent layers laminated can be efficiently produced by the pressure bonding technique.

A method for producing an orally administrable edible agent of laminate film form according to fifth and sixth aspects of the invention is characterized in that one resin film to be delaminated in the resin film delaminating step in the first or second aspects of the invention and one resin film to be delaminated in the resin film delaminating and removing step in the second aspect of the invention each are previously subjected to release treatment at least on a surface provided with the orally administrable edible agent layers. This allows one resin film only to be delaminated smoothly and reliably.

A method for producing an orally administrable edible agent of laminate film form according to seventh and eighth aspects of the invention is characterized in that one resin film to be delaminated in the resin film delaminating step in the third or fourth aspects of the invention and one resin film to be delaminated in the resin film delaminating and removing step in the fourth aspect of the invention each are previously subjected to release treatment on both a front surface provided with the orally administrable edible agent layers and an opposite back surface, and the other resin film retaining the orally administrable edible agent layers without being delaminated in the resin film delaminating step or the resin film delaminating and removing step is previously subjected to release treatment at least on a back surface provided with no orally administrable edible agent layer. This allows one resin film only to be delaminated smoothly and reliably. Further, the method is carried out in the batch manner by forming the rolled film in the intermediate step, and thus, even if the orally administrable agent layer-formed resin film is wound into a roll to form the rolled film, no orally administrable edible agent layer adheres to the back surface to allow the rolled film to be unwound smoothly.

A method for producing an orally administrable edible agent of laminate film form according to a ninth aspect of the invention is characterized in that, in any one of the first to fourth aspects of the invention, a pressure is 0.05 to 1.5 MPa when the resin films are joined so that the orally administrable edible agent layer surfaces face each other and are pressurized at the back surfaces. This allows the orally administrable edible agent layers to be reliably bonded and integrated as a preparation of film form while being kept in a layered form without excessive compaction of the orally administrable edible agent layers.

A method for producing an orally administrable edible agent of laminate film form according to a tenth aspect of the invention is characterized in that, in any one of the first to fourth aspects of the invention, a temperature of the orally administrable edible agent layer is 50° C. to 180° C. when the resin films are joined so that the orally administrable edible agent layer surfaces face each other and are pressurized at the back surfaces. This allows the orally administrable edible agent layers to be slightly softened and reliably bonded together without being molten. Excessive heating may cause the orally administrable edible agent layers to be molten to prevent the layered form from being kept, prevent functions of the orally administrable edible agent layers such as a covering layer, a drug layer, and a support layer from being served, and prevent physicochemical properties that the administrable agent aims such as an elution property, a mucosa adhesion property, resistance to moisture during storage as designed from being achieved. Pressurization at the limited temperature range described above avoids such disadvantages, and allows the orally administrable edible agent layers to be reliably bonded into the layered form.

A method for producing an orally administrable edible agent of laminate film form according to an eleventh aspect of the invention is characterized in that, in the tenth aspect of the invention, after the orally administrable edible agent layers are bonded and before the resin film is delaminated from the bonded orally administrable edible agent layers, the bonded orally administrable edible agent layers are cooled to a temperature 10° C. or more lower than the temperature of the orally administrable edible agent layers when the resin films are joined so that the orally administrable edible agent layer surfaces face each other and are pressurized at the back surfaces, and the temperature of the cooled orally administrable edible agent layers is kept higher than 0° C. This allows one resin film only to be delaminated smoothly and reliably, and allows the orally administrable edible agent layers to be reliably retained on the other intended resin film.

A method for producing an orally administrable edible agent of laminate film form according to a twelfth aspect of the invention is characterized in that, in the tenth aspect of the invention, each of the bonded orally administrable edible agent layers contains an edible thermoplastic substance. This allows the orally administrable edible agent layers to be bonded together more reliably at the heating temperature in pressurizing as described in the tenth aspect of the invention.

The edible thermoplastic substance may include, as described in a thirteenth aspect of the invention, at least one selected from the group consisting of amylose, carboxymethyl cellulose potassium, carboxymethyl cellulose sodium, carboxymethyl cellulose calcium, alkyl ester alginate, sodium alginate, ethylcellulose, eudragit, carboxymethylethylcellulose, carboxymethyl starch, carboxymethyl cellulose, agar, gelatin, shellac, dextran, dextrin, starch, tragacanth, hydroxyethylcellulose, hydroxypropylcellulose, hydroxypropylmethylcellulose, hydroxypropylmethylcellulose phthalate, polyvinylpyrrolidone, methacrylic acid copolymer, and methylcellulose phthalate.

A method for producing an orally administrable edible agent of laminate film form according to a fourteenth aspect of the invention is characterized in that, in any one of the first to fourth aspects of the invention, a thickness of each of the orally administrable edible agent layers formed by pressure bonding the orally administrable edible agent layers is 1 to 300 μm. This allows a rapid-dissoluble orally administrable edible agent of film form to be formed that can be taken without water for an orally administrable agent, and allows an orally administrable edible agent to be formed that provides no uncomfortable feeling if orally applied for a patch applied to oral mucosa.

A method for producing an orally administrable edible agent of laminate film form according to a fifteenth aspect of the invention is characterized in that, in any one of the first to fourth aspects of the invention, the bonded orally administrable edible agent layers are self-supporting laminated films. Further, a method for producing an orally administrable edible agent of laminate film form according to a sixteenth aspect of the invention is characterized in that, in the fifteenth aspect of the invention, the two resin films sandwiching the bonded orally administrable edible agent layers are finally delaminated from the bonded orally administrable edible agent layers. The laminated films are self supporting to facilitate delamination of the two resin films sandwiching the laminated films, thereby preventing the agent from being taken with the resin film by mistake to provide an orally administrable edible agent that can be easily taken.

A pressure bonding apparatus of an orally administrable edible agent of laminate film form according to a seventeenth aspect of the invention is characterized by comprising: a pair of press rolls that draw two resin films each provided with an orally administrable edible agent layer having a predetermined thickness on a surface thereof so that orally administrable edible agent layer surfaces face each other, and pressurize the resin films at back surfaces; a delamination roll having a diameter of 6 cm or less disposed in a position in a direction substantially conforming to a tangential direction at a pressurization zone of said pair of press rolls in a delivery direction (in a downstream region) of said pair of press rolls; a winding shaft that draws and delaminates only one of said two resin films sandwiching the plural orally administrable edible agent layers conveyed from said pair of press rolls to the delamination roll and bonded together, in a direction different from a conveying direction from said pair of press rolls to said delamination roll, along a peripheral surface of said delamination roll; and a conveyance mechanism that conveys, when said one resin film is delaminated, the other film retaining the plural orally administrable edible agent layers, in said conveying direction from the pair of press rolls to the delamination roll.

According to the seventeenth aspect of the invention, the orally administrable edible agent of film form has strength sufficient to form a self-supporting film to cause the orally administrable edible agent layers to adhere to one resin film to be delaminated, which tends to cause trouble that the orally administrable edible agent layers cannot be retained on the other intended resin film. However, in the downstream region (in the delivery direction) of the pair of press rolls, the delamination roll is disposed in the position in the direction substantially conforming to the tangential direction at the pressurization zone of the pair of press rolls, the delamination roll has the small diameter of 6 cm or less, and one resin film is drawn and delaminated in the direction different from the conveying direction from the pair of press rolls to the delamination roll, thereby allowing the orally administrable edible agent to be reliably retained on the other intended resin film to provide a pressure bonding apparatus with high productivity.

A pressure bonding apparatus of an orally administrable edible agent of laminate film form according to an eighteenth aspect of the invention is characterized in that, in the seventeenth aspect of the invention, the delamination roll is rotatably disposed so as to rotate with movement of the above described one resin film.

According to the eighteenth aspect of the invention, the delamination roll is rotated with the movement of one resin film to be delaminated to thereby allow smooth delamination of the other resin film only.

A pressure bonding apparatus of an orally administrable edible agent of laminate film form according to a nineteenth aspect of the invention is characterized in that, in the seventeenth or eighteenth aspects of the invention, the winding shaft is disposed in a position where the above described one resin film only is drawn at an angle of 45° or more to the conveying direction of the other resin film with the delamination roll as a starting point.

According to the nineteenth aspect of the invention, the winding shaft is disposed in the predetermined position to thereby allow smoother and reliable delamination of one resin film only.

A pressure bonding apparatus of an orally administrable edible agent of laminate film form according to a twentieth aspect of the invention is characterized in that, in the seventeenth aspect of the invention, the apparatus further comprises: a pair of unwinding rolls that respectively feed the two resin films each provided with the orally administrable edible agent layer having the predetermined thickness on the surface thereof to the pair of press rolls; and a winding roll that winds up, with the above described one resin film being delaminated by the delamination roll, the other resin film retaining the plural orally administrable edible agent layers conveyed by the conveyance mechanism, and the unwinding roll and the winding roll have substantially the same dimension and structure and are interchangeable.

According to the twentieth aspect of the invention, the winding roll and the unwinding roll are interchangeable, and thus the resin film retaining the plural orally administrable edible agent layers obtained by the pressure bonding apparatus of the invention is wound up on the winding roll to once form a rolled film, and the resulting rolled film is used again as it is as a starting material of the pressure bonding apparatus to be pressure bonded with another rolled film, thereby allowing the orally administrable edible agent of film form having the multilayer structure to be easily formed in a batch manner.

Specifically, the resin film retaining the plural orally administrable edible agent layers obtained by the pressure bonding apparatus of the invention is once wound up on the winding roll in the batch manner to form the rolled film, the resulting rolled film is set as it is in the pressure bonding apparatus as a source rolled film wound up on the unwinding roll, another source rolled film that is the resin film retaining a single or a plurality of orally administrable edible agent layer/layers of the same ingredient or different ingredients wound up on the unwinding roll is similarly set in the pressure bonding apparatus, the two resin films unwound from the rolled films are joined so that the orally administrable edible agent layers face each other, drawn into a nip between the pair of press rolls, and pressurized at the back surfaces, thereby allowing the orally administrable edible agent of film form having the multilayer structure including the multiple orally administrable edible agent layers bonded and laminated to be efficiently and extremely easily produced in the batch manner. This invention provides a pressure bonding apparatus having a flexibility to be well able to produce an orally administrable edible agent of film form having a multilayer structure of many types suitable for various purposes by a combinations of various batch type operations as needed.

A pressure bonding apparatus of an orally administrable edible agent of laminate film form according to a twenty-first aspect of the invention is characterized in that, in the seventeenth aspect of the invention, the apparatus further comprises: a slitter that cuts, with the above described one resin film being delaminated by the delamination roll, the other resin film retaining the plural orally administrable edible agent layers conveyed by the conveyance mechanism into narrow strips in parallel with the conveying direction; and a plurality of winding reels each of which individually winds up each of the narrow strips obtained by cutting the other resin film retaining the plural orally administrable edible agent layers into a plurality of pieces by the slitter, and the plurality of winding reels are arranged so that their winding shaft portions except their flange portions are staggered backward and forward without gaps.

According to the twenty-first aspect of the invention, in individually winding up each of the narrow strips obtained by cutting and dividing the other resin film retaining the plural orally administrable edible agent layers into a plurality of pieces by the slitter on the winding reel corresponding to each of the strips, the winding shaft portions of the winding reels are staggered backward and forward without gaps, and there is no need for providing spaces between the narrow strips of the resin film cut and divided into the plurality of pieces. This allows the resin film cut and divided into the narrow strips to be individually and smoothly wound up on the winding reels without causing distortion, wrinkles or cracks in the orally administrable edible agent layers retained on the resin film.

A pressure bonding apparatus of an orally administrable edible agent of laminate film form according to a twenty-second aspect of the invention is characterized in that, in the seventeenth aspect of the invention, the apparatus further comprises: a slitter that can switch between an ON state where said one resin film is delaminated by said delamination roll, and said other resin film retaining the plural orally administrable edible agent layers conveyed by said conveyance mechanism is cut into narrow strips in parallel with the conveying direction, and an OFF state where said other resin film is passed through without being cut; a shaft that supports a plurality of winding reels each of which individually winds up each of the narrow strips obtained by cutting the other resin film retaining the plural orally administrable edible agent layers into a plurality of pieces by the slitter in the ON state; and a winding roll that winds up said other resin film retaining the plural orally administrable edible agent layers conveyed by said conveyance mechanism through said slitter in the OFF state without being cut, and said shaft that supports the plurality of winding reels and said winding roll are interchangeable.

According to the twenty-second aspect of the invention, the shaft that supports the winding reels each of which individually winds up each of the plurality of narrow strips of the resin film by operating the slitter can be replaced with the winding roll that winds up a wide resin film retaining the plural orally administrable edible agent layer in the batch manner. This allows easy switching as required between a cutting and dividing operation of the resin film by the slitter, and a pressure bonding operation in the batch manner without the slitter being operated, thereby providing a pressure bonding apparatus of an orally administrable edible agent of film form that is generally compact and requires a small installation area.

A pressure bonding apparatus of an orally administrable edible agent of laminate film form according to a twenty-third aspect of the invention is characterized in that, in the twenty-first or twenty-second aspect of the invention, the shaft that supports the plurality of winding reels is supported at both ends thereof by frames, one end of the shaft can be supported so as to be cantilevered by one of the frames, and the other frame that supports the other end of the cantilevered shaft can be brought down and stood up.

According to the twenty-third aspect of the invention, one end of the shaft is cantilevered by the frame, and the frame that supports the other end is brought down to allow the winding reels supported by the shaft to be easily and quickly mounted to or removed from the shaft with the shaft being cantilevered, and eliminate the need for moving the entire shaft that supports the plurality of winding reels, thereby extremely improving workability.

A pressure bonding apparatus of an orally administrable edible agent of laminate film form according to a twenty-fourth aspect of the invention is characterized in that, in the twenty-first or twenty-second aspects of the invention, each of the winding reels is rotatably supported by the shaft, side walls of each winding reel are pressed by a spring disposed at one end of the shaft and biased toward the other end of the shaft, and an biasing force of the spring causes rotation of the shaft to be transmitted to the winding reels.

According to the twenty-fourth aspect of the invention, the biasing force of the spring that presses the winding reel side walls causes rotation of the shaft to be transmitted to the winding reels, and thus adjusting the biasing force of the spring allows the degree of slip of the winding reels with respect to the shaft to be adjusted.

Specifically, increasing the biasing force of the spring reduces the slip between the winding reels and the shaft to increase the transmission of the rotation of the shaft to the winding reels and thus increase a winding force of the resin film by the winding reels. On the other hand, reducing the biasing force of the spring tends to cause the slip between the winding reels and the shaft to reduce the transmission of the rotation of the shaft to the winding reels and thus reduce the winding force of the resin film by the winding reels. In this way, the winding force can be easily controlled depending on variation of a winding amount of the resin film on the winding reels, thereby eliminating the need for installing an expensive control device.

When the structure including the slitter and the winding reels in the twenty-first aspect of the invention are essential in the invention, the following descriptions may be made. Specifically, a pressure bonding apparatus of an orally administrable edible agent of laminate film form according to the invention is characterized by comprising: a pair of press rolls that draw two resin films each provided with an orally administrable edible agent layer having a predetermined thickness on a surface so that orally administrable edible agent layer surfaces face each other, and pressurize the resin films at back surfaces; a resin film delamination mechanism including a delamination roll disposed in a position in a direction substantially conforming to a tangential direction at a pressurization zone of the pair of press rolls in a delivery direction of the pair of press rolls, and a winding shaft that draws and delaminates only one of the two resin films sandwiching the plural orally administrable edible agent layers conveyed from the pair of press rolls to the delamination roll and bonded together, in a direction different from a conveying direction from the pair of press rolls to the delamination roll, along a peripheral surface of the delamination roll; a conveyance mechanism that conveys, when the above described one resin film is delaminated, the other film retaining the plural orally administrable edible agent layers, in the conveying direction from the pair of press rolls to the delamination roll; a slitter that cuts, with the above described one resin film being delaminated by the delamination roll, the other resin film retaining the plural orally administrable edible agent layers conveyed by the conveyance mechanism into narrow strips in parallel with the conveying direction; and a plurality of winding reels each of which individually winds up each of the narrow strips obtained by cutting the other resin film retaining the plural orally administrable edible agent layers into a plurality of pieces by the slitter, the plurality of winding reels being arranged so that their winding shaft portions except their flange portions are staggered backward and forward without gaps.

Similarly, when the structure including the slitter and the winding reels in the twenty-second aspect of the invention are essential in the invention, the following descriptions may be made. Specifically, a pressure bonding apparatus of an orally administrable edible agent of laminate film form according to the invention is characterized by comprising: a pair of press rolls that draw two resin films each provided with an orally administrable edible agent layer having a predetermined thickness on a surface so that orally administrable edible agent layer surfaces face each other, and pressurize the resin films at back surfaces; a resin film delamination mechanism including a delamination roll disposed in a position in a direction substantially conforming to a tangential direction at a pressurization zone of the pair of press rolls in a delivery direction of the pair of press rolls, and a winding shaft that draws and delaminates one of the two resin films sandwiching the plural orally administrable edible agent layers conveyed from the pair of press rolls to the delamination roll and bonded together, in a direction different from a conveying direction from the pair of press rolls to the delamination roll, along a peripheral surface of the delamination roll; a conveyance mechanism that conveys, when the above described one resin film is delaminated, the other film retaining the plural orally administrable edible agent layers, in the conveying direction from the pair of press rolls to the delamination roll; a slitter that can switch between an ON state where the above described one resin film is delaminated by the delamination roll, and the other resin film retaining the plural orally administrable edible agent layers conveyed by the conveyance mechanism is cut into narrow strips in parallel with the conveying direction, and an OFF state where the other resin film is passed through without being cut; a shaft that supports a plurality of winding reels each of which individually winds up each of the narrow strips obtained by cutting the other resin film retaining the plural orally administrable edible agent layers into a plurality of pieces by the slitter in the ON state; and a winding roll that winds up the other resin film retaining the plural orally administrable edible agent layer conveyed by the conveyance mechanism through the slitter in the OFF state without being cut, the shaft that supports the plurality of winding reels and the winding roll being interchangeable.

DETAILED DESCRIPTION OF THE INVENTION

Figure 1:
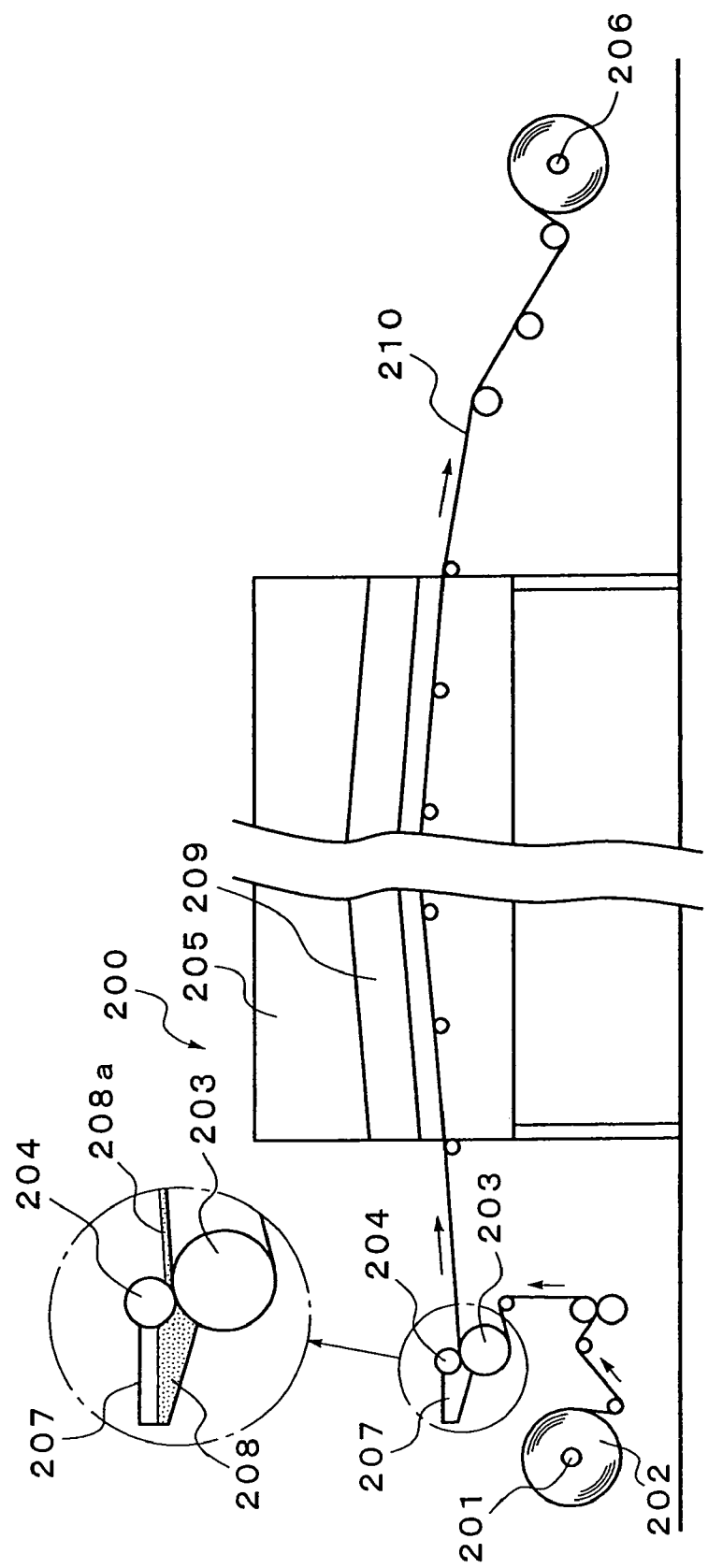
FIG. 1 illustrates an example of a coating apparatus for forming an orally administrable edible agent layer on a resin film by coating.

In forming an orally administrable edible agent layer (hereinafter referred to as "an administrable agent layer") having a predetermined thickness on a surface of a resin film, a coating apparatus 200 shown in FIG. 1 can be preferably used. The coating apparatus 200 guides a resin film 202 set on a resin film unwinding roll 201 into a drying oven 205 through a nip between a guide roll 203 and a doctor roll 204, and winds up the resin film 202 on a resin film winding roll 206, thereby continuously moving the resin film 202. In the meantime, an administrable agent layer preparation solution 208 contained in a dam portion 207 for supplying the administrable agent layer preparation solution is spread on the resin film, and at this time, a clearance between the resin film 202 on the guide roll 203 and the doctor roll 204 is adjusted to a predetermined dimension to obtain a predetermined coating amount (see the partial enlarged view). A coating layer 208a on the resin film 202 thus formed passes through the drying oven 205 and is dried by hot air uniformly blown from a hot air blowing device 209, and a resin film 210 provided with an administrable agent layer is wound up on the winding roll 206 into a roll.

Then, the administrable agent layer-formed resin film 210 wound up on the winding roll 206 into the roll is mounted to the unwinding roll 201 again, the administrable agent layer preparation solution 208 of the same or different ingredient is supplied to the dam portion 207 for coating and drying again, and the resin film is wound up on the winding roll 206, thereby producing a resin film including laminated two administrable agent layers. Repeating such coating and drying steps several times allows a thickness of the administrable agent layer of the same ingredient to be increased or allows a plurality of administrable agent layers of various ingredients to be formed.

However, as described herein-above, since a coating amount of the administrable agent layer preparation solution becomes inaccurate and drying time increases as the number of coating and drying steps increases, the coating and drying steps are preferably repeated twice or three times at most, and more preferably once. A thickness of the administrable agent layer formed on the surface of the resin film in one coating step is preferably about 1 to 300 μm. A coating thickness in one coating step larger than 300 μm excessively increases the drying time to reduce productivity.

The coating apparatus 200 in FIG. 1 is used to perform a single coating step or a plurality of coating steps with the same ingredient or different ingredients to produce a resin film 210 provided with an administrable agent layer having a predetermined thickness on the surface thereof. The administrable agent layer-formed resin film 210 of various types thus produced each are wound up on the winding roll 206 into a roll to form a rolled film, and then a pressure bonding apparatus 10 of the invention as shown in FIG. 2 is used to pressure bond two administrable agent layer-formed resin films and form an administrable agent layer of film form having a multilayer structure including laminated many thin layers on the resin film.

Figure 2:
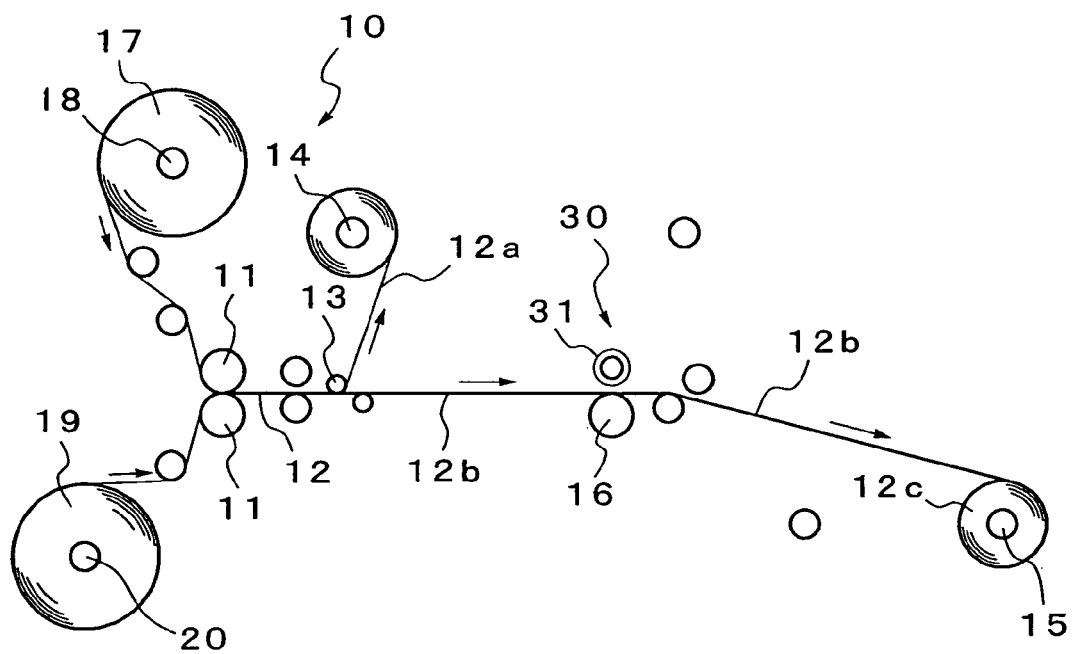
FIG. 2 illustrates an embodiment of a pressure bonding apparatus according to the invention.

FIG. 2 shows an embodiment of the pressure bonding apparatus 10 according to the invention, which includes a pair of press rolls 11 and 11 that draw joined two resin films produced, for example, using the coating apparatus 200 as shown in FIG. 1 and each provided with the administrable agent layer having the predetermined thickness on the surface thereof so that the administrable agent layers face each other, and pressurize the resin films at back surfaces; a delamination roll 13 that delaminates one 12a of the two resin films 12 (an intermediate pressure bonded product) sandwiching plural administrable agent layers conveyed from the press rolls and bonded together; a winding shaft 14 that winds up the delaminated film; and a winding roll 15 that winds up a plural administrable agent layers-retained resin film 12b (a pressure bonded product) left after the delamination.

The winding roll 15 is used as a drive roll, one of the press rolls 11 and 11 is used as a drive roll, and another drive roll 16 is disposed between the delamination roll 13 and the winding roll 15. These three drive rolls constitute a conveyance mechanism of the plural administrable agent layers—retained resin film, and can convey the plural administrable agent layers-retained resin film 12b delivered from the press rolls 11 and 11 to the winding roll 15.

Figure 3:
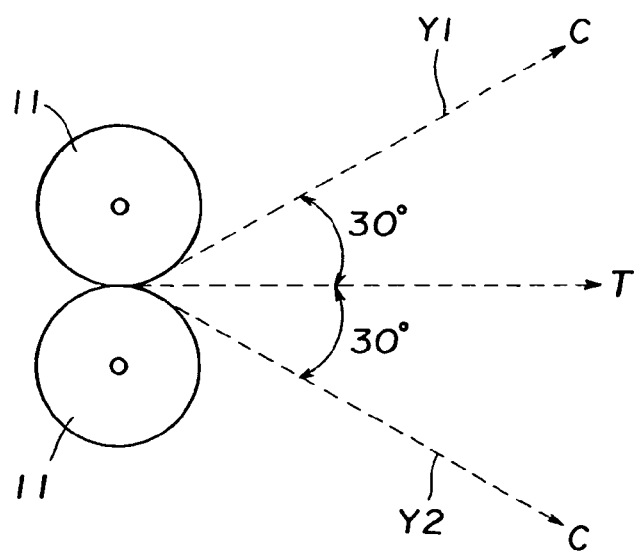
FIG. 3 illustrates a conveying direction of an intermediate pressure bonded product delivered from press rolls of the pressure bonding apparatus in FIG. 2.

A conveying direction of the plural administrable agent layers-retained resin film 12b by the conveyance mechanism conforms to a tangential direction at a pressurization zone of the pair of press rolls 11 and 11 as shown in FIG. 2, but the conveying direction may nearly or substantially, even not accurately, conform to the tangential direction so that, as shown in FIG. 3, displacement between the tangential direction T and the conveying direction C is 30° or less, preferably 15° or less, and more preferably 10° or less. In other words, the conveying direction may be within a range between the arrow Y1 and the arrow Y2 in FIG. 3.

The delamination roll 13 is disposed in a position along the conveying direction of the plural administrable agent layers-retained resin film delivered from the press rolls 11 and 11, specifically in a position within a range between the arrow Y1 and the arrow Y2 in FIG. 3 in the direction substantially conforming to the tangential direction at the pressurization zone of the pair of press rolls 11 and 11 in a delivery direction of the pair of press rolls 11 and 11. Delamination can be carried out by winding up one 12a of the two resin films 12 sandwiching the bonded plural administrable agent layers by the winding shaft 14 that draws one 12a of the two resin films 12 in a direction different from the conveying direction of the plural administrable agent layers-retained resin film 12b. The delamination roll 13 is rotatably disposed so as to rotate with movement of the resin film 12a to be delaminated.

Figure 4:
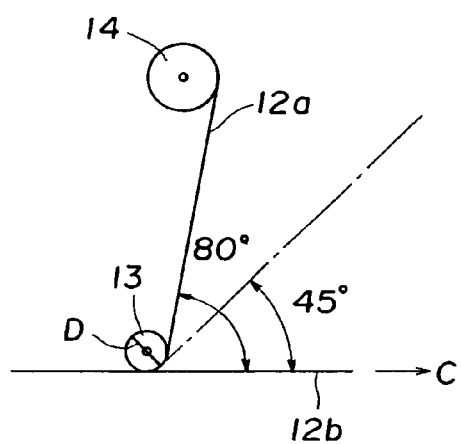
FIG. 4 illustrates a positional relationship between a delamination roll and a winding shaft for a film to be delaminated in FIG. 2.

The plural administrable agent layers have strength sufficient to form a self-supporting film to cause the administrable agent layers to adhere to one resin film 12a to be delaminated, thereby sometimes preventing the administrable agent layers from being retained on the other (another) resin film 12b. Thus, in the invention, as shown in FIG. 4, the delamination roll 13 has a diameter D of 6 cm or less, preferably 5 cm or less, and one resin film is delaminated with a sharp angle along a peripheral surface of the delamination roll 13 having the small diameter to allow the plural administrable agent layers to be reliably retained on the other intended resin film 12b. The winding shaft 14 that winds up the resin film 12a to be delaminated is preferably disposed in a position where the resin film 12a to be delaminated is drawn at an angle of 45° or more, preferably 60° or more to the conveying direction C of the plural administrable agent layers-retained resin film 12b with the delamination roll 13 as a starting point. In an example shown in FIG. 4, the winding shaft 14 is disposed in a position where the delaminated film 12a is drawn at an angle of about 80° to the conveying direction C.

An operation of the pressure bonding apparatus 10 according to the invention shown in FIG. 2 is as described below. A rolled film 17 of the resin film provided with the administrable agent layer on the surface (for example, a rolled film wound on the winding roll 206 in FIG. 1) is set on an upper unwinding roll 18 of the pressure bonding apparatus 10, and another rolled film 19 is set on a lower unwinding roll 20. These rolled films 17 and 19 are unwound at predetermined speeds, joined together, namely superposed one on another, so that administrable agent layer surfaces face each other, and passed through a nip between the pair of press rolls 11 and 11 to pressurize the resin films at back surfaces to bond the administrable agent layers together.

In pressurizing by the press rolls 11 and 11, the press rolls 11 and 11 or guide rolls in previous steps to the press rolls 11 and 11 are heated by an electric heater or a steam heater included in the rolls so that a temperature of the administrable agent layer during pressurization is 50° C. to 180° C., preferably 50° C. to 80° C. The temperature needs to be selected according to types of the resin film or types of materials used for the administrable agent layers, and a temperature at which the administrable agent layers are slightly softened and easily bonded is preferable. An excessively high temperature should be avoided because it may cause the administrable agent layers to be molten and cause volatilization and bumping of solvents in the administrable agent layers, and an excessively low temperature may cause insufficient bonding. A pressurizing pressure by the press rolls is 0.05 to 1.5 MPa, preferably 0.1 to 0.7 MPa. An excessive pressure causes the administrable agent layer to spread, which unpreferably affects quantitative accuracy per unit area. An excessively low pressure causes insufficient bonding.

The intermediate pressure bonded product 12 having passed through the press rolls 11 and 11 has a structure in which both surfaces are coated with the resin films and the plural administrable agent layers are bonded and laminated between the resin films. At the time when the intermediate pressure bonded product 12 passes through the delamination roll 13, only the resin film 12a covering an upper surface is delaminated, and the delaminated resin film 12a is wound up on the delaminated film winding shaft 14 to continuously delaminate the resin film 12a from the intermediate pressure bonded product 12.

After the administrable agent layers are bonded and before the resin film 12a is delaminated from the bonded plural administrable agent layers, the bonded administrable agent layers are preferably cooled to a temperature 10° C. or more lower than the temperature of the administrable agent layers when pressurized by the press rolls 11 and 11 (when the resin films are joined so that the administrable agent layer surfaces face each other, and are pressurized at the back surfaces). Excessive cooling is unnecessary, and the temperature of the cooled administrable agent layers is kept higher than 0° C., preferably higher than a normal temperature (or a room temperature). Thus, the cooling may be natural cooling by heat dissipation resulting from providing a long distance between the press rolls 11 and 11 and the delamination roll 13, or active cooling by blowing air at room temperature such as sterilized air or cooled air. This allows the resin film 12a to be reliably and continuously delaminated from the intermediate pressure bonded product 12.

The pressure bonded product 12b thus obtained, that is, the resin film retaining the plural administrable agent layers on the surface thereof is wound up on the winding roll 15 into a roll to form a plural administrable agent layers retaining rolled film 12c, that is, a rolled film retaining the orally administrable edible agent of laminate film form according to the invention.

Another administrable agent layer may be laminated on the plural administrable agent layers-retained resin film 12b (pressure bonded product) in the following manner. Specifically, the plural administrable agent layers-retained rolled film 12c obtained as described above may be removed from the winding roll 15 and set on the upper unwinding roll 18 in FIG. 2, and another plural administrable agent layers—retained rolled film 12c similarly formed may be set on the lower unwinding roll 20 to repeat the same operation as the pressure bonding operation described above. At this time, the winding roll 15 and the unwinding rolls 18 and 20 may have substantially the same dimension and structure and be interchangeable, and thus the rolled film 12c wound up on the winding roll 15 may be set as it is in the positions of the reference numerals 18 and 20 and used as a starting material of the pressure bonding apparatus 10 again to repeat the pressure bonding operations several times, thereby allowing an orally administrable agent of film form having a multilayer structure, that is, an orally administrable edible agent of laminate film form according to the invention including a larger number of administrable agent layers laminated to be easily realized in a batch manner.

Figure 5:
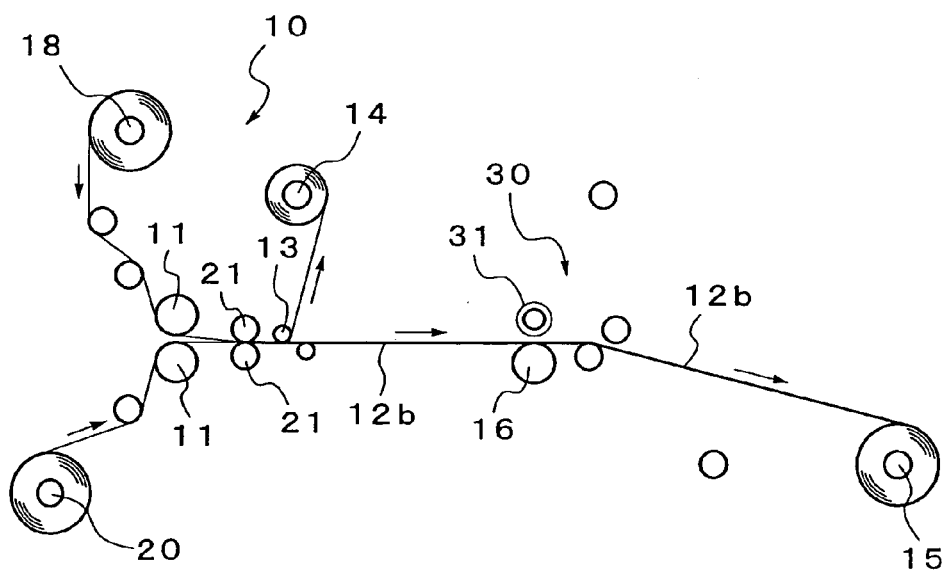
FIG. 5 illustrates an example of an operation of the pressure bonding apparatus in FIG. 2.

When the two resin films retaining the administrable agent layers are passed through the nip between the press rolls 11 and 11 and pressure bonded, air trapped between the two resin films causes poor adhesion. In this case, as shown in FIG. 5, a pair of rolls 21 and 21 disposed downstream of the press rolls 11 and 11 are closed by narrowing a gap therebetween, and the press rolls 11 and 11 are opened by widening a gap therebetween without stopping the operation of the pressure bonding apparatus 10. This operation causes the air trapped between the two resin films to be easily forced out by the closed rolls 21 and 21 and removed. After the air is removed, the press rolls 11 and 11 are closed and the rolls 21 and 21 are opened to return to a normal pressure bonding operation as shown in FIG. 2.

A powder brake and a powder clutch conventionally used may be used for controlling tension of the resin film when unwound from the unwinding rolls 18 and 20 and wound up on the winding roll 15 in the pressure bonding apparatus 10 shown in FIG. 2. Specifically, for the powder brake (not shown) disposed in the unwinding rolls 18 and 20, control is performed so as to reduce a braking force by reducing a voltage applied to the powder brake to gradually reduce tension as a winding diameter reduces. On the other hand, for the powder clutch (not shown) disposed in the winding roll 15, a winding diameter is automatically monitored to control transmission power of the powder clutch at a voltage according to the winding diameter to keep constant winding tension. Specifically, control is performed so as to increase the voltage applied to the powder clutch and increase the transmission power of the powder clutch as the winding diameter increases.

The above described pressure bonding operation for pressure bonding the resin films retaining the administrable agent layers by the press rolls 11 and 11 is efficiently performed by using as wide a resin film as possible, cutting and dividing the resin film into predetermined narrow strips, and then supplying the strips to a preparation step where the strips are punched out into predetermined shapes. For this purpose, in the embodiment of the pressure bonding apparatus 10 according to the invention shown in FIG. 2, a slitter 30 is disposed that cuts the plural administrable agent layers—retained resin film 12b into narrow strips in parallel with the conveying direction, in a position along the conveying direction of the plural administrable agent layers-retained resin film 12b, after only the resin film 12a covering the upper surface of the intermediate pressure bonded product delivered from the press rolls 11 and 11 is delaminated by the delamination roll 13.

Figure 6:
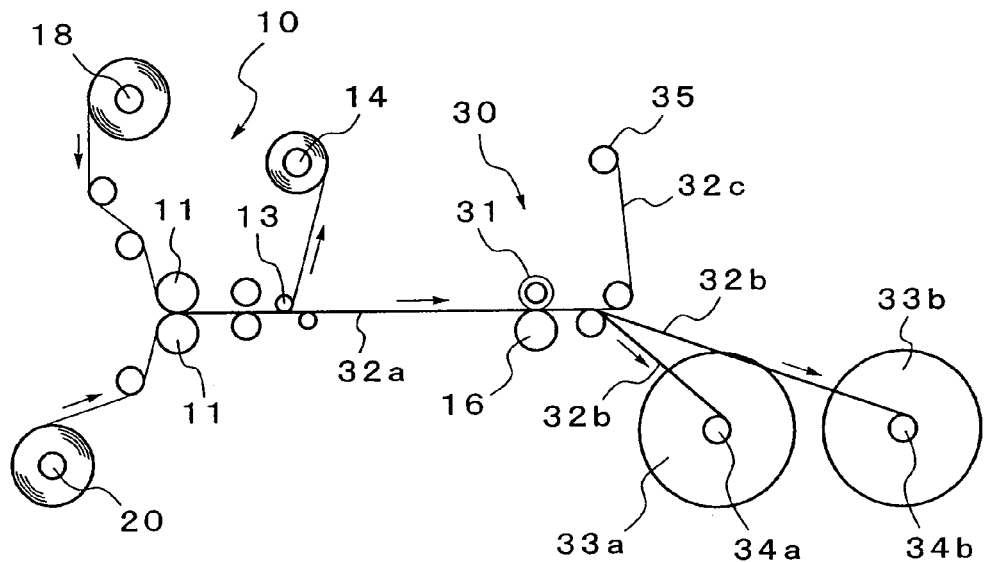
FIG. 6 illustrates an embodiment with a slitter of the pressure bonding apparatus in FIG. 2 being operated.

The slitter 30 is configured in combination with the drive roll 16 in an embodiment in FIG. 6, and a plurality of disk-like blades 31 disposed so as to face the drive roll 16 are vertically movable. Specifically, as shown in FIGS. 2 and 5, when the wide plural administrable agent layers-retained resin film 12b is wound up on the winding roll 15, the disk-like blades 31 are placed in an upper position, and a gap between the disk-like blades 31 and the drive roll 16 therebelow is widened and opened so that the slitter 30 does not operate. On the other hand, when the plural administrable agent layers-retained resin film to be a final pressure bonded product is cut into narrow strips, as shown in FIG. 6, the disk-like blades 31 move downward, the gap between the disk-like blades 31 and the drive roll 16 therebelow is closed, and a wide final pressure bonded product (wide pressure bonded product) 32a that passes through the gap is cut and divided into narrow pressure bonded products 32b. The plurality of narrow pressure bonded products 32b cut and divided into narrow strips are individually wound up on a plurality of winding reels 33a and 33b, respectively.

A width of the plural administrable agent layers of the wide pressure bonded product 32a is, for example, 460 mm, and when this product is cut into twelve narrow pressure bonded products 32b each having a width of 36 mm by the slitter 30, thirteen disk-like blades 31 are arranged in parallel with 36 mm spacing along the width of the administrable agent layers. Cutting chips 32c at both side edges of the administrable agent layers are wound up on a chip winding shaft 35 and removed.

Figure 7:
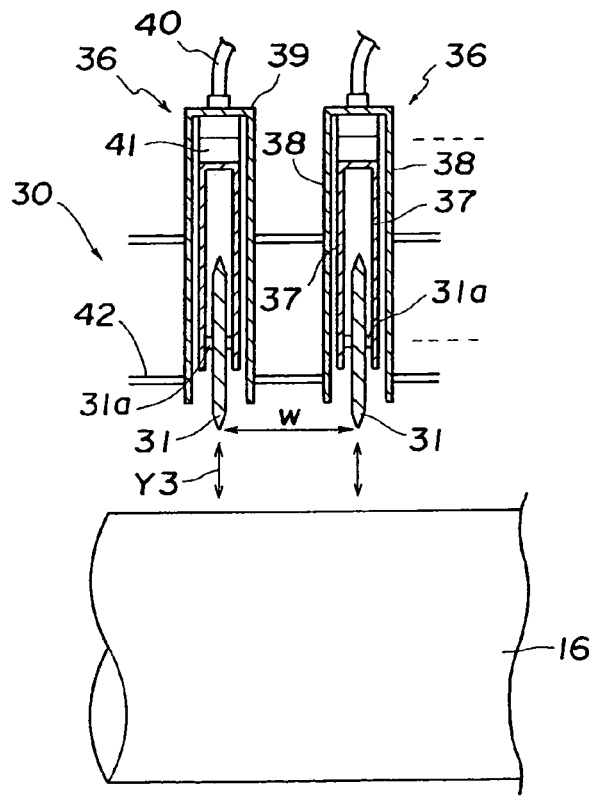
FIG. 7 is a sectional view of an example of a structure of the slitter.
Figure 8:
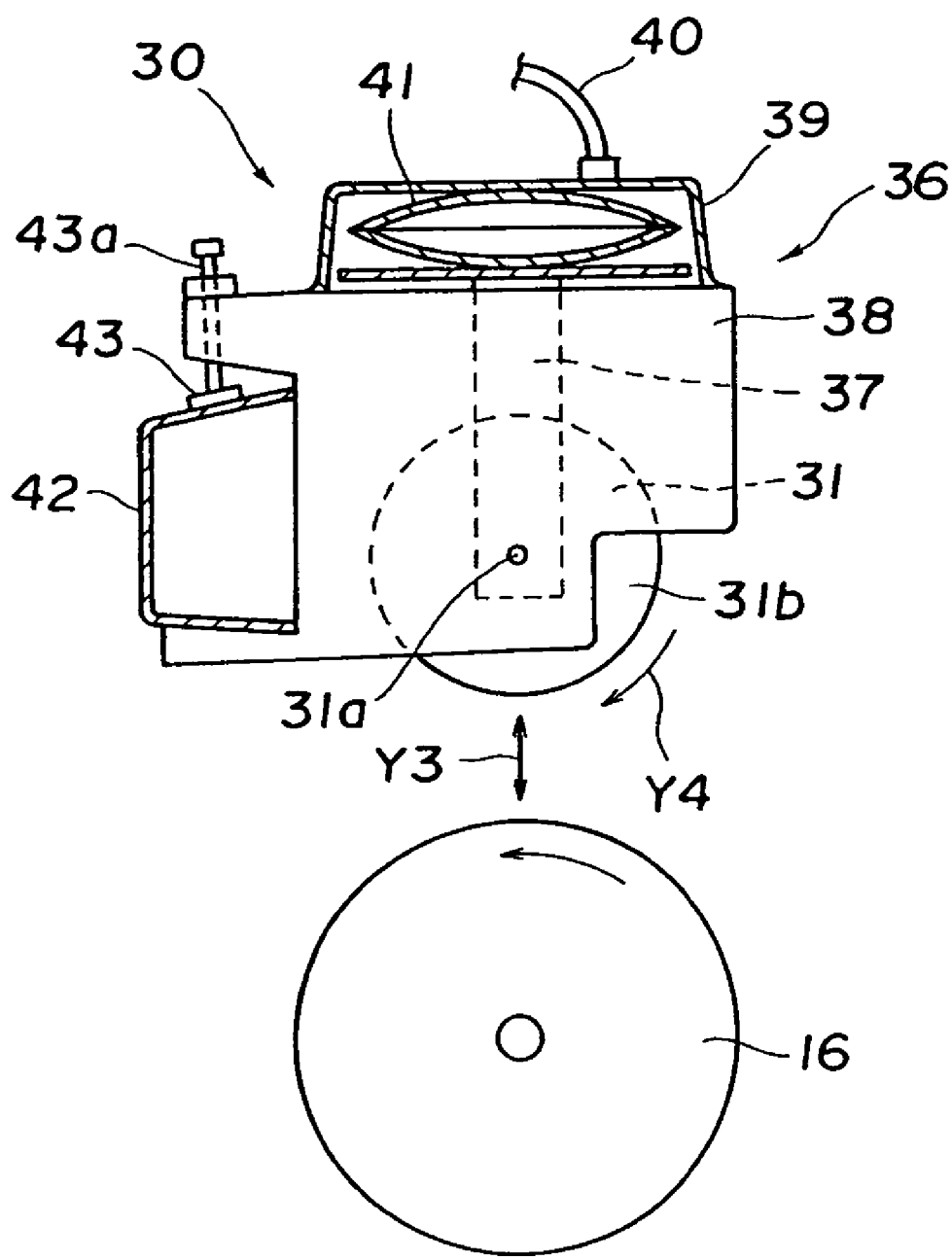
FIG. 8 is an elevational view, partially broken away, of an example of a structure of the slitter.

The slitter 30 has a structure in which a plurality of (for example, thirteen) slitter units 36 and 36 as shown in FIGS. 7 and 8 are arranged evenly spaced apart along the width of the administrable agent layers, that is, a width of the drive roll 16. Each slitter unit 36 includes one disk-like blade 31, and blades 31 of adjacent slitter units are arranged in parallel with each other with, for example, 36 mm spacing (w in FIG. 7). In FIG. 7, two slitter units 36 and 36 only arranged in parallel along the width of the drive roll 16 are shown for simplicity of the drawing. In each slitter unit 36, a rotation axis 31a of the disk-like blade 31 is rotatably supported by a bearing 37, the blade 31 and the bearing 37 are vertically movably (the arrow Y3) housed between two side walls 38 and 38, and a portion 31b of the blade extending to a forward lower end in a rotational direction (the arrow Y4 in FIG. 8) of the blade 31 protrudes from the side wall 38. An air bag housing portion 39 is disposed in a top of the side wall 38, which houses a flexible air bag 41 connected to an air tube 40, so that the bearing 37 and the disk-like blade 31 vertically move according to inflation and contraction of the air bag 41. A fixture 43 for securing each slitter unit 36 to a slitter frame 42 disposed in parallel with an axial direction of the drive roll 16 is mounted to a rear end of the side wall 38 (on a side where the pressure bonded products cut into narrow strips are delivered from the slitter 30), and the slitter units 36 are individually mounted and secured to predetermined positions of the slitter frame 42 by fastening screws 43a and arranged in parallel.

An operation of the slitter 30 shown in FIGS. 7 and 8 is as described below. When the slitter 30 is not operated, air in the air bag 41 is removed via the air tube 40 and the air bag 41 is flat. At this time, the blade is held in an upper lifted position, and the gap between the blade and the drive roll 16 is widened (see FIG. 2). Specifically, the slitter is in an OFF state where the resin film is passed through without being cut, and the wide intermediate pressure bonded product 12b conveyed is wound up on the winding roll 15 without being cut.

When air is introduced from the air tube 40 into the air bag 41, the air bag 41 is inflated to force the bearing 37 downward, thereby causing the blade 31 to abut and be pressed against the peripheral surface of the drive roll 16 (see FIG. 6). Namely, the slitter enters an ON state where the resin film is cut into narrow strips in parallel with the conveying direction. In this state, the wide intermediate pressure bonded product 32a conveyed is cut into the narrow pressure bonded products 32b each having a width corresponding to a width w between the blades 31 and 31 of the adjacent slitter units 36 and 36.

For the narrow pressure bonded products 32b cut into twelve strips each having a width of 36 mm by the slitter 30, six narrow pressure bonded products 32b in an odd-numbered row are individually wound up on six winding reels 33a coaxially supported by a shaft 34a placed forward, and six narrow pressure bonded products 32b in an even-numbered row are individually wound up on six winding reels 33*b* coaxially supported by a shaft 34*b* placed backward (see FIG. 6).

Figure 9:
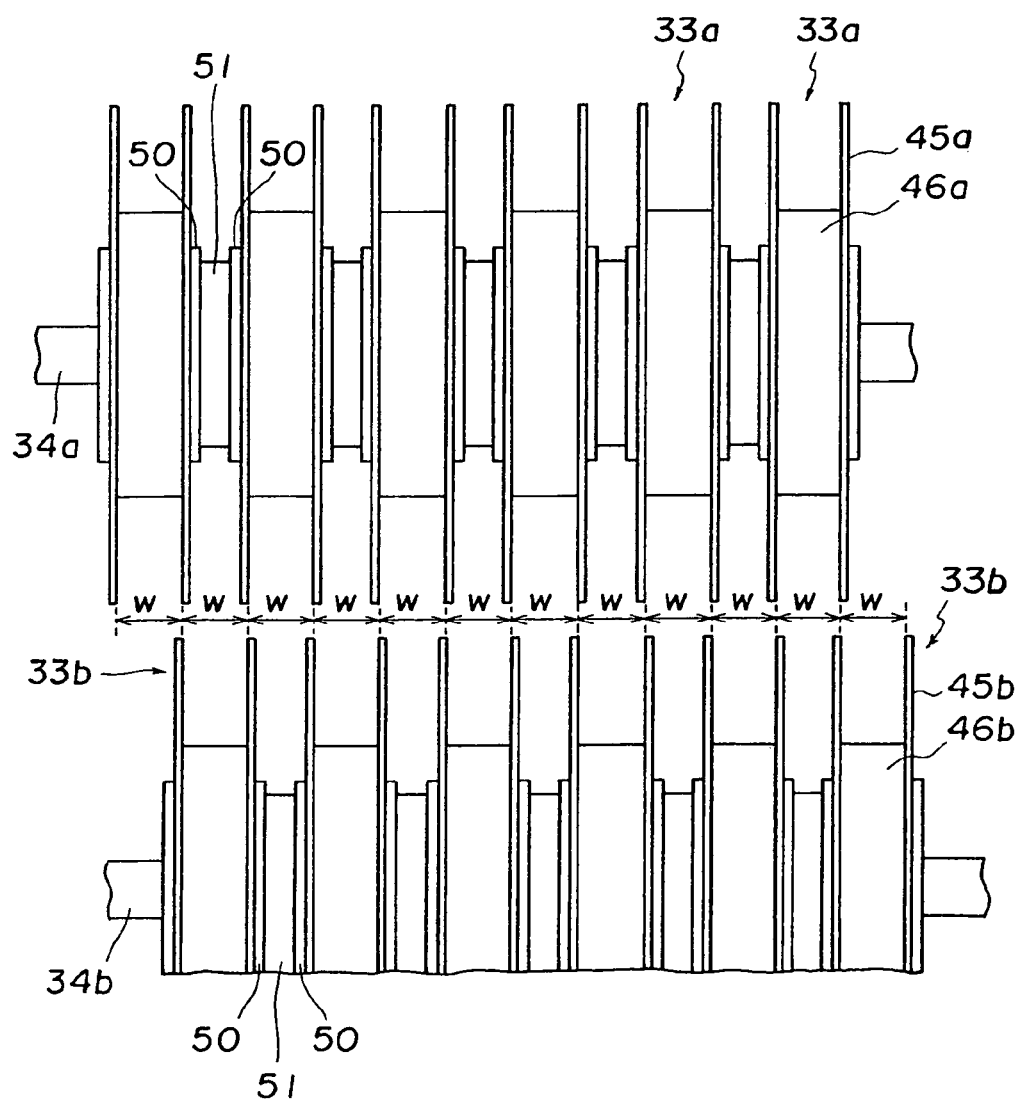
FIG. 9 illustrates a state where winding shaft portions of a plurality of winding reels supported by two shafts are staggered backward and forward without gaps.

The six winding reels 33*a* supported by the shaft 34*a* and the six winding reels 33*b* supported by the shaft 34*b* are staggered backward and forward in two rows as shown in FIG. 9. At this time, reel plates 50 and 50 each having a predetermined width and a spacer 51 are inserted between adjacent winding reels 33 and 33 supported by the shafts 34*a* and 34*b* to allow winding shaft portions 46*a* except flange portions 45*a* of the winding reels 33*a* of the shaft 34*a* in a front row and winding shaft portions 46*b* except flange portions 45*b* of the winding reels 33*b* of the shaft 34*b* in a back row to be arranged in a staggered fashion without gaps. A width of the winding shaft 46 is equal to the width w (36 mm) of one narrow pressure bonded product to be wound up thereon. Thus, the twelve narrow pressure bonded products 32*b* cut and divided with the width of 36 mm by the slitter 30 are conveyed in parallel with each other along the width thereof to the winding reels 33 and individually wound up on different winding reels 33, without increasing the total width of the twelve products (432 mm). This effectively eliminates distortion, wrinkles or cracks of the administrable agent layers of the narrow pressure bonded products 32*b* as generated in the case where narrow pressure bonded products are individually wound up on different winding reels while increasing spacing in width between adjacent narrow pressure bonded products cut and divided.

In the example in FIGS. 6 and 9, the shafts 34*a* and 34*b* that support the plurality of winding reels 33 are arranged in the backward and forward two rows, but may be arranged in backward and forward three or more rows according to the number of winding reels 33.

Figure 10:
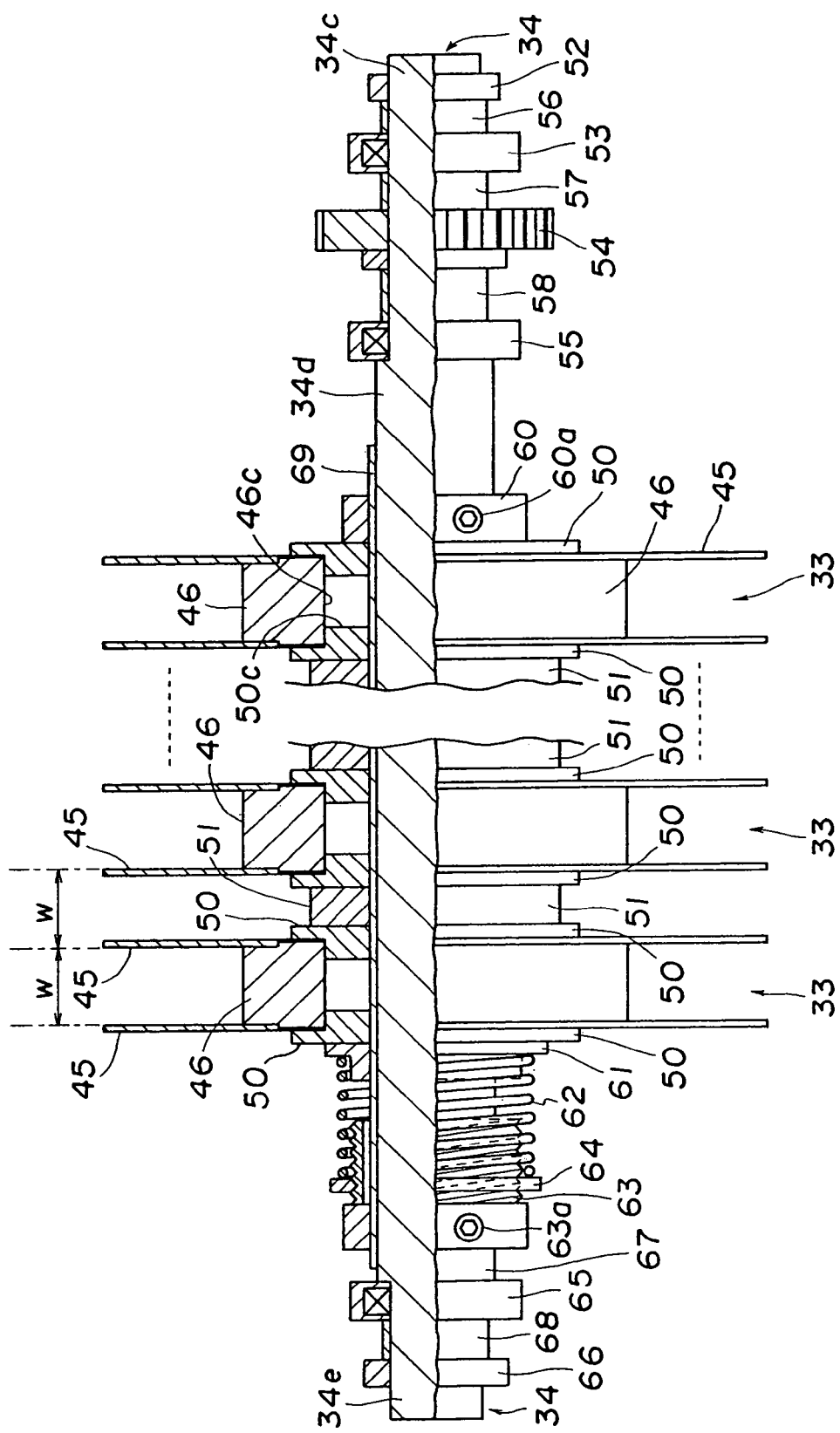
FIG. 10 illustrates a mechanism for setting the plurality of winding reels on the shaft.

A mechanism for setting the plurality of winding reels 33 on the shaft 34 is shown in FIG. 10. In FIG. 10, an upper half of the shaft 34 is shown in a sectional view, and a lower half is shown in a front view, respectively. To a small diameter portion 34*c* at one end (a right end in the drawing) of the shaft 34, a stopper 52, a bearing 53, a gear 54 and a bearing 55 that are all of the annular shape are fitted and secured in order from the right via collars 56, 57 and 58, respectively. To a large diameter portion 34*d* continuing from the small diameter portion 34*c* of the shaft, an annular stopper 60 is fitted to a right end thereof and secured by a securing bolt 60*a*. To a left side of the stopper 60, a reel plate 50, a winding reel 33, a reel plate 50, a spacer 51, a reel plate 50, a winding reels 33, a reel plate 50, a spacer 51 . . . that are all of the annular shape are successively fitted in this order, and for example, six winding reels 33 are fitted. To a left side of the reel plate 50 that positions the sixth winding reel 33, a spring bracket 61, a spring 62, and a slotted bushing 63 having a threaded outer periphery that are all of the annular shape are fitted in this order, and the slotted bushing 63 is secured by a securing bolt 63*a*. A press screw 64 is fitted to the slotted bushing 63 and screwed on thread grooves in the outer periphery thereof. Further, to a small diameter portion 34*e* at the other end (a left end in the drawing) of the shaft 34, a bearing 65 and a stopper 66 that are both of the annular shape are fitted and secured via collars 67 and 68.

A key 69 constituted by an elongated protrusion is formed in a longitudinal direction of the large diameter portion 34*d* of the shaft, and key grooves formed in inner peripheral surfaces of the reel plate 50, the spacer 51, the spring bracket 61 and the slotted bushing 63 that are annular fitting members fitted to the shaft engage the key 69 to ensure that rotation of the shaft 34 is transmitted to these annular fitting members.

The winding reel 33 includes the winding shaft portion 46 made of polytetrafluoro ethylene (Teflon®) and the flange portion 45 made of aluminum alloy extending radially from both side surfaces of the winding shaft portion, and a pair of annular reel plates 50 and 50 sandwiching the winding reel 33 from both sides are in surface contact with side surfaces of the winding shaft portion 46. An annular protrusion 50*c* having a small diameter that fits in a center hole 46*c* of the annular winding shaft portion 46 is formed in the reel plate 50 at a portion closer to the center thereof, and the annular protrusion 50*c* is caused to fit in the center hole 46*c* of the winding shaft portion 46 to allow easy and reliable positioning of the winding reel 33.

Each winding reel 33 is rotatably supported by the shaft 34 via contact surfaces (slide surfaces) between the winding shaft portion 46 and the annular reel plates 50 and 50 sandwiching the winding shaft portion 46, the side wall of the winding shaft portion 46 of each winding reel 33 is pressed by the spring 62 disposed at the left end of the shaft 34 and urged to the right of the shaft 34, and an biasing force of the spring 62 causes the rotation of the shaft 34 to be transmitted to the winding reel 33 via the annular reel plates 50 and 50. This action will be described later in detail.

As shown in FIG. 9, in order for the winding shaft portions 46*a* of the winding reels 33*a* in the front row and the winding shaft portions 46*b* of the winding reels 33*b* in the back row to be staggered without gaps, the sum w of the width of the spacer 51 in FIG. 10 and the widths of the reel plates 50 and 50 and the reel flange portions 45 and 45 disposed on both sides of the spacer 51 are equal to the width w of the reel winding shaft portion 46 (that is, the width of the narrow intermediate pressure bonded product).

Figure 11:
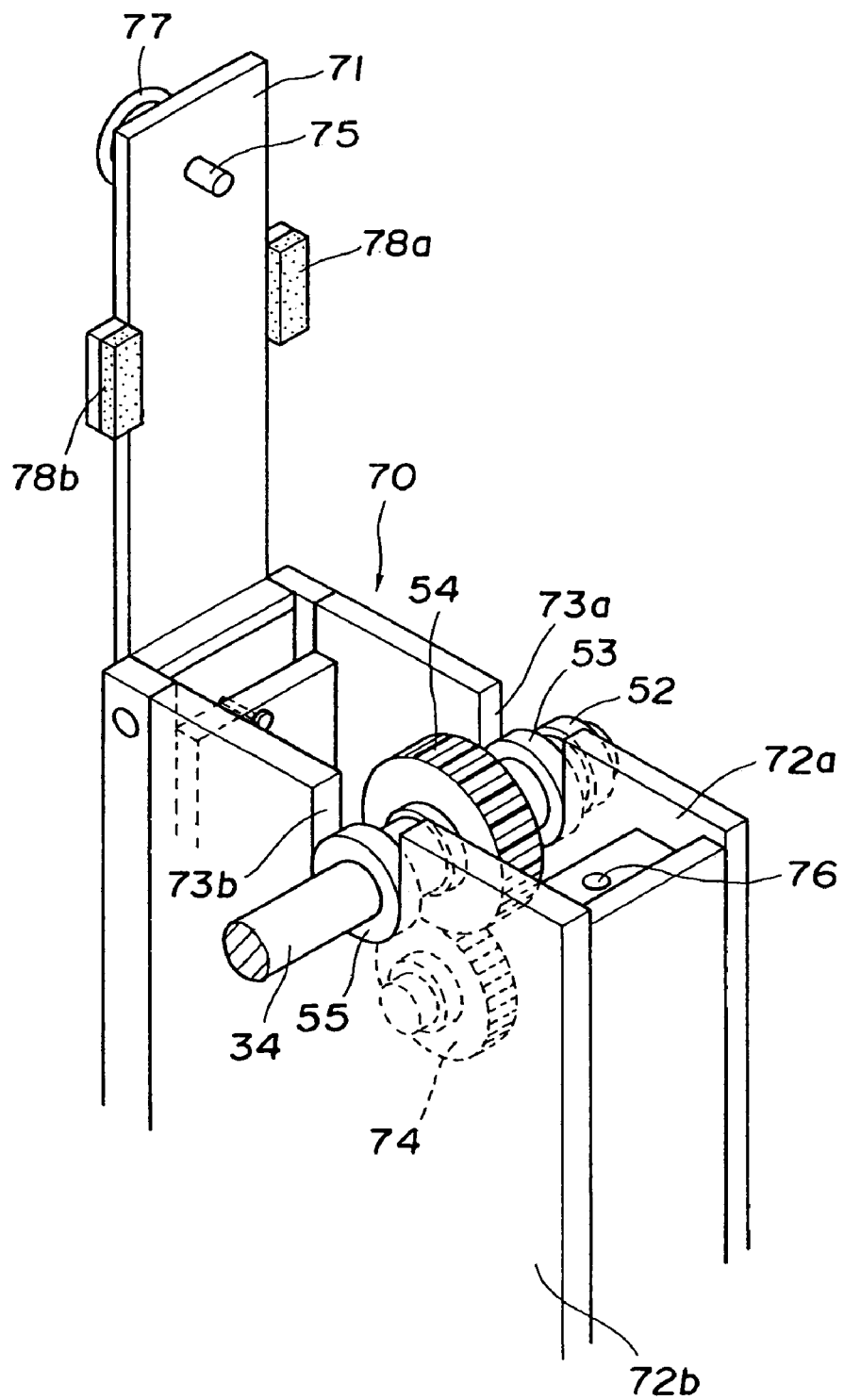
FIG. 11 is a perspective view of a right bearing frame that supports a right end of the shaft.
Figure 12:
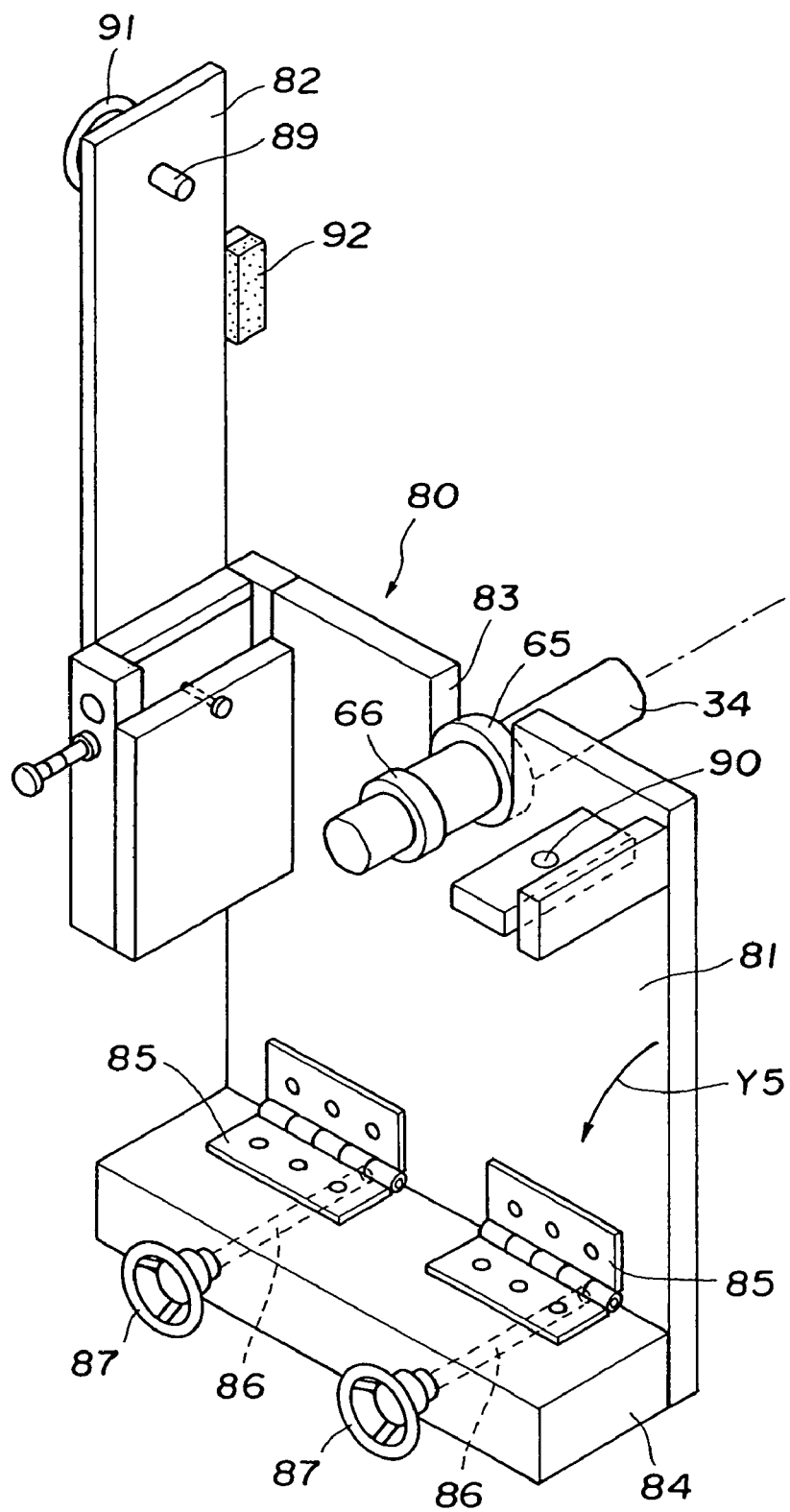
FIG. 12 is a perspective view of a left bearing frame that supports a left end of the shaft.

A bearing frame for supporting the shaft 34 in a predetermined position is shown in FIGS. 11 and 12. FIG. 11 shows a right bearing frame 70 that supports the right end of the shaft 34 shown in FIG. 10, which generally has a vertically long box shape and includes an openable lid 71 in a top opening surface. U-shaped notches 73*a* and 73*b* are formed in top portions of two opposite side walls 72*a* and 72*b*, and a drive gear 74 driven by an unshown motor is disposed between the side walls 72*a* and 72*b* at portions lower than these U-shaped notches. FIG. 11 shows a state where the lid 71 is opened and the right end of the shaft 34 is placed on the bearing frame 70. The two bearings 53 and 55 mounted to the shaft 34 are fitted into the two U-shaped notches 73*a* and 73*b* of the bearing frame 70 to cause the gear 54 to engage the drive gear 74, thereby causing the rotation of the drive gear 74 to be transmitted to the shaft 34 via the gear 54. The lid 71 can be closed by bringing down the lid 71 to close the top opening surface and inserting a setscrew 75 into a screw hole 76 to rotate a setscrew handle 77. At this time, bearing pressing tools 78*a* and 78*b* mounted to both sides of the lid 71 are used to press top portions of the bearings 53 and 55 fitted in the U-shaped notches 73*a* and 73*b* so as to prevent the bearings from being removed from the U-shaped notches.

FIG. 12 shows a left bearing frame 80 that supports the left end of the shaft 34, which includes one side wall 81 and a lid 82. A U-shaped notch 83 is formed in a top portion of the side wall 81, and the lid 82 is mounted to the side wall 81 in an openable manner. A base plate 84 abuts at a side surface thereof against a bottom portion of the side wall 81, and the side wall 81 and the base plate 84 are connected by hinges 85 and 85. The side wall 81 can be held in a vertically standing manner as shown in FIG. 12 by passing a setscrew 86 through a through hole formed in the base plate 84 to rotate a screw handle 87 and causing a tip of the setscrew 86 to be screwed into a screw hole 88 (see FIG. 13) formed in a lower portion of the side wall 81. FIG. 12 shows a state where the lid 82 is opened and the left end of the shaft 34 is placed on the bearing frame 80, and one bearing 65 mounted to the shaft 34 is fitted in the U-shaped notch 83 of the bearing frame 80. The lid 82 can be closed by bringing down the lid 82 in this state and inserting a setscrew 89 into a screw hole 90 to rotate a setscrew handle 91. At this time, a bearing pressing tool 92 mounted to a side of the lid 82 is used to press a top portion of the bearing 65 fitted in the U-shaped notch 83 so as to prevent the bearing from being removed from the U-shaped notch.

Figure 13:
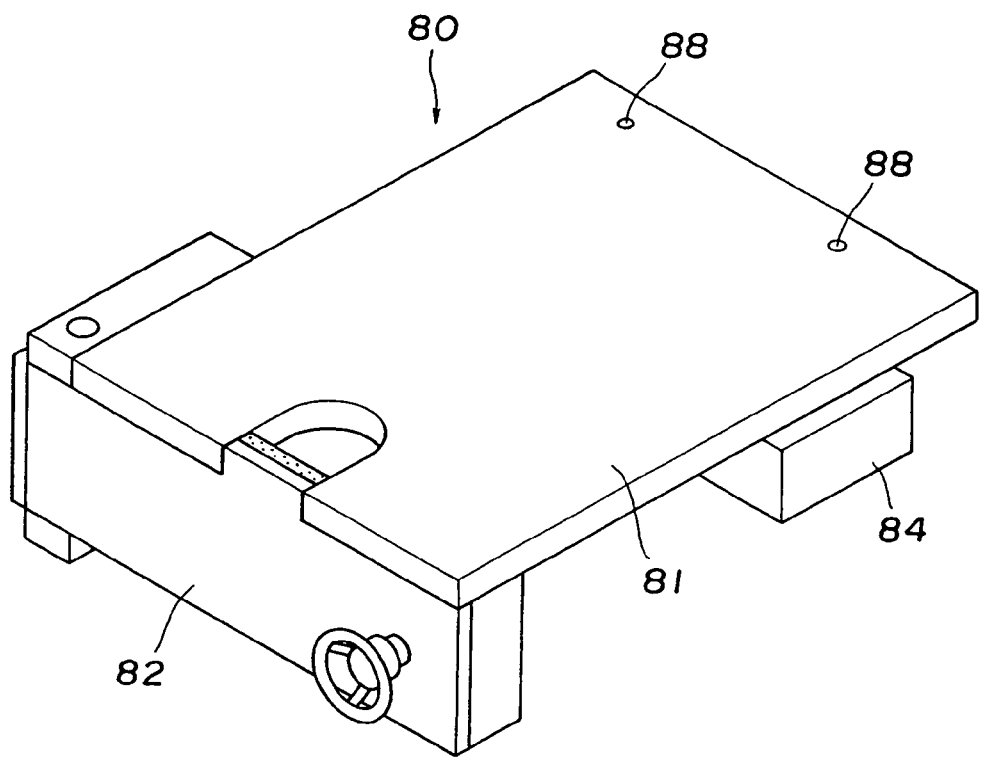
FIG. 13 is a perspective view of a state where the left bearing frame in FIG. 12 is brought down.

The side wall 81 of the left bearing frame 80 in FIG. 12 can be brought down in a direction of the arrow Y5, and a state where the side wall 81 is brought down is shown in FIG. 13. The side wall 81 can be brought down by rotating the setscrew handle 91 (FIG. 12) in a direction such that the setscrew 89 (FIG. 12) is disengaged and removed from the screw hole 90 to open the lid 82, then rotating the screw handle 87, and bending the side wall 81 at the hinges 85 (FIG. 12) through unscrewing of the setscrew 86 from the screw hole 88.

An operation of the shaft 34 on which the plurality of winding reels 33 are set as shown in FIG. 10 will be now described below. When the both ends of the shaft 34 are placed on the bearing frames 70 and 80 in FIGS. 11 and 12, respectively, the drive gear 74 disposed in the right bearing frame 70 (FIG. 11) engages the gear 54 of the shaft to cause the rotation of the drive gear 74 to be transmitted to the shaft 34. The rotation of the shaft is reliably transmitted to each annular fitting member by the engagement between the key 69 and the key grooves, and the annular fitting members such as the reel plates 50, the spacers 51, the spring bracket 61, and the slotted bushing 63 reliably rotate with the rotation of the shaft 34.

However, the winding shaft portion 46 of the winding reel 33 is made of polytetrafluoro ethylene having a low coefficient of friction, which causes a slide on the contact surfaces (the surfaces shown in bold lines FIG. 10) between the winding shaft portion 46 and the reel plates 50 and 50 sandwiching the winding shaft portion 46 from the both sides, thereby preventing the rotation of the shaft 34 from being transmitted to the winding reel 33 as it is.

The transmission of the rotation of the shaft 34 to the winding reel 33 varies depending on the degree of slide between the winding shaft portion 46 of the reel and the reel plates 50. The degree of slide can be adjusted by strength of the spring 62 fitted to the left side of the shaft 34. Specifically, when the press screw 64 screwed in the slotted bushing 63 is pushed toward the right of the shaft 34, the spring 62 presses and urges the reel plates 50 and the spacers 51 toward the right of the shaft. When the biasing force of the spring 62 is strong, the slide between the winding shaft portion 46 of the reel and the reel plates 50 is reduced, and the rotation of the shaft 34 is easily transmitted to the winding reel 33. On the other had, when the biasing force of the spring 62 is weak, the slide between the winding shaft portion 46 of the reel and the reel plates 50 is increased, and the rotation of the shaft 34 is prevented from being transmitted to the winding reel 33 to allow free rotation.

The narrow pressure bonded products cut and divided by the slitter 30 are individually wound up on the winding reels 33, and thus the winding diameter increases as the winding proceeds, which reduces the number of rotation of the winding reel 33 required for winding up the narrow pressure bonded products with the same length. The plurality of winding reels 33 supported by one shaft 34 do not always have the same winding diameters, but sometimes have different winding diameters. In an embodiment as shown in FIG. 10, adjusting the biasing force of the spring 62 allows the individual winding reels 33 to be rotated at a free number of rotation corresponding to variations of the winding diameters of the winding reels 33.

At the time when the winding operation of the narrow pressure bonded products 32b on the plurality of winding reels 33 set on the shaft 34 is completed, the drive gear 74 of the right bearing frame 70 in FIG. 11 is stopped to stop rotation of the shaft 34, and the winding reels 33 are removed from the shaft 34. In removing the winding reels 33, the lid 82 of the left bearing frame 80 in FIG. 12 is opened to bring down the side wall 81 to cantilever the shaft 34 by the right bearing frame 70 with the right end of the shaft 34 being set on the right bearing frame 70 in FIG. 11. In this cantilevered state, the winding reels 33 can be successively removed together with the reel plate 50 and the spacer 51 by successively removing the stopper 66, the bearing 65, the slotted bushing 63, the spring 62, and the spring bracket 61 that are the annular fitting members from the left end of the shaft 34. In this manner, the shaft 34 can be cantilevered to successively remove the winding reels 33 from the shaft 34, which eliminates the need for an operation for removing the heavy shaft 34 supporting the plurality of winding reels 33 by a plurality of operators, thereby allowing the plurality of winding reels 33 to be easily and quickly removed by one operator.

In the embodiment of the pressure bonding apparatus of the invention shown in FIGS. 2 and 6, the wide pressure bonded product is wound up on the winding roll 15 when the slitter 30 is not operated, and the narrow pressure bonded products are individually wound up on the plurality of winding reels 33 when the slitter 30 is operated to cut and divide the narrow pressure bonded product into the narrow pressure bonded products. In this case, the shaft 34 that supports the winding reels 33 and the winding roll 15 are interchangeably set on the bearing frames 70 and 80 shown in FIGS. 11 and 12, thereby allowing a pressure bonding operation of the wide pressure bonded product and a cutting and dividing operation into the narrow pressure bonded products to be switched as required.

Figure 14:
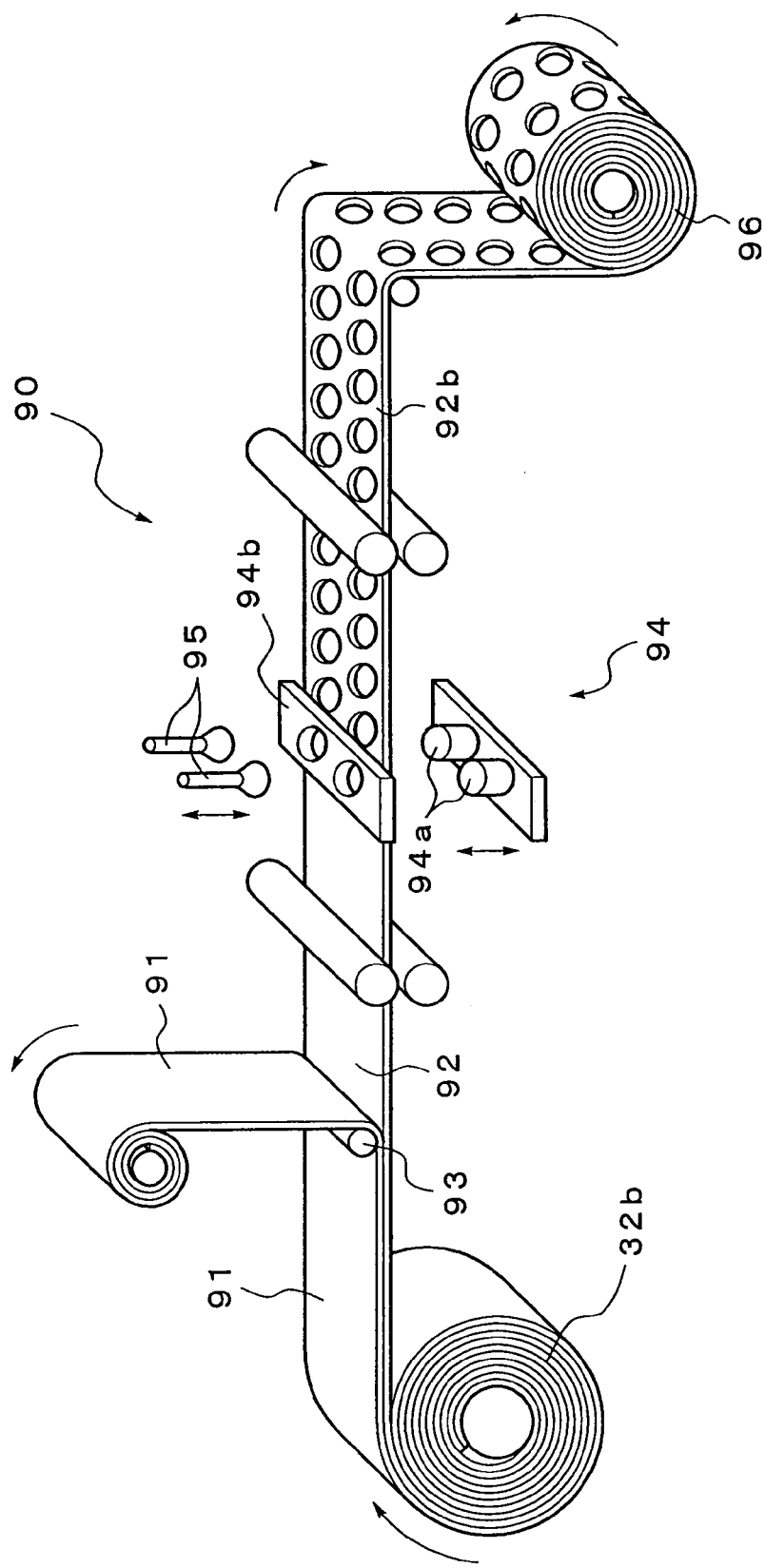
FIG. 14 is a perspective view of an embodiment of an administrable agent forming apparatus that punches out a final pressure bonded product obtained by the invention into a predetermined shape.
Figure 15:
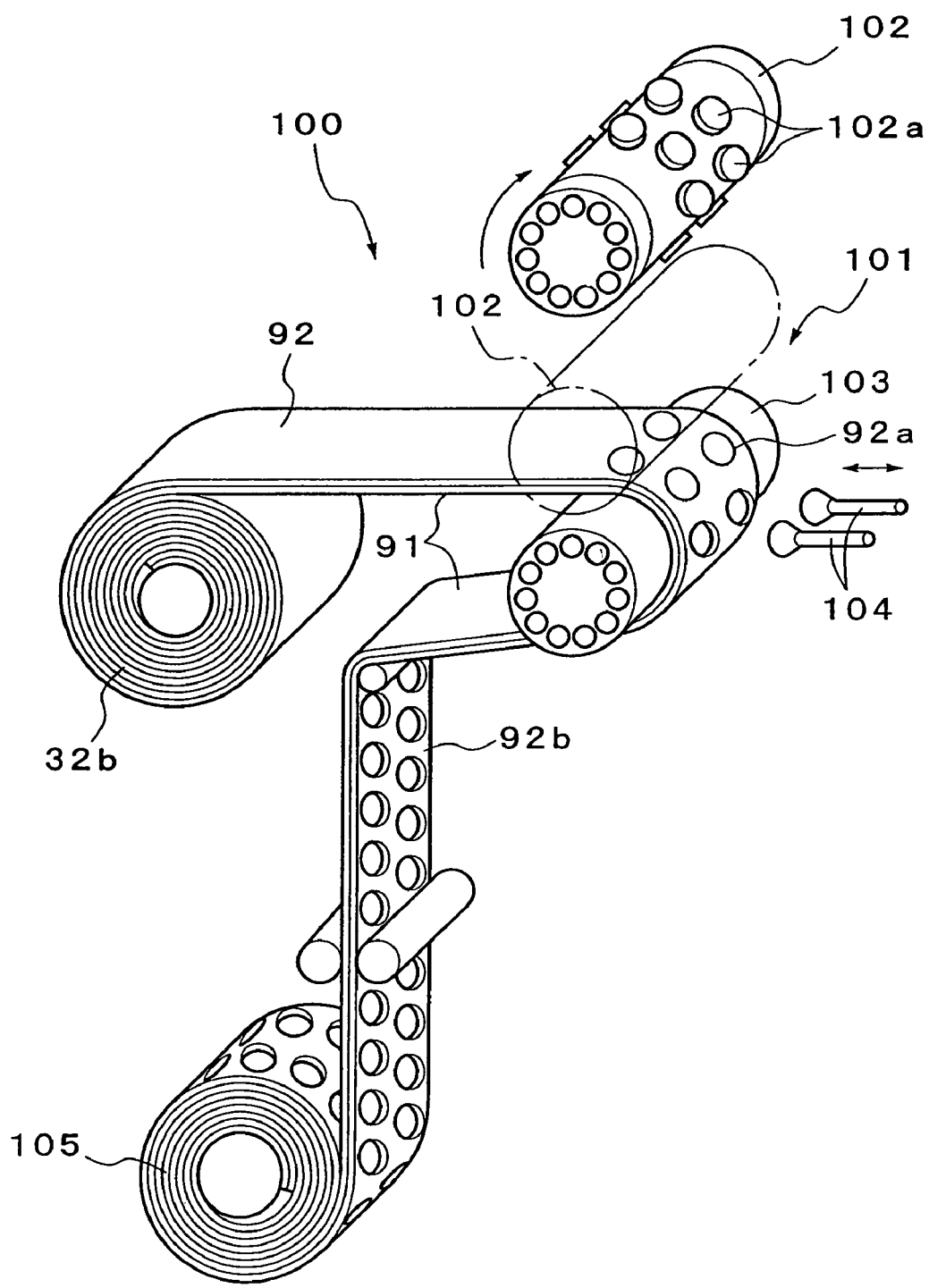
FIG. 15 is a perspective view of another embodiment of an administrable agent forming apparatus that punches out a final pressure bonded product obtained by the invention into a predetermined shape.

The narrow pressure bonded product 32b (36 mm wide) thus cut may be formed into, for example, a circular administrable agent of laminate film form using an administrable agent forming apparatus as shown in FIGS. 14 and 15.

In an administrable agent forming apparatus 90 in FIG. 14, the narrow pressure bonded product 32b wound on the reels 33a and 33b in FIG. 6 in rolls, that is, a pressure bonded product in which one of resin films is delaminated, and plural administrable agent layers 92 are retained on a surface of a remaining resin film 91 is intermittently unwound, and the remaining resin film 91 is delaminated by a film delamination roll 93 to leave the administrable agent layers 92 only. Then, the plural administrable agent layers 92 are punched out into a circle, for example, with a diameter of 15 mm by a punching device 94. The punching device 94 includes cutting blades 94a that vertically move and a securing plate 94b having through holes through which the cutting blades pass. When the administrable agent layers 92 intermittently moved stop at a position of the punching device 94, the cutting blades 94a move upward and pass through the through holes of the securing plate 94b to punch out the administrable agent layers 92 into circles with the diameter of 15 mm. The circular administrable agent layers punched out are sucked by suction pads 95 disposed above the securing plate 94b, and dropped onto a conveyer (not shown) and fed to a packaging step. Administrable agent layer chips 92b after the circular administrable agent layers are removed are wound up as a chip winding roll 96.

In an administrable agent forming apparatus 100 in FIG. 15, the narrow pressure bonded product 32b wound on the reels 33a and 33b in FIG. 6 in rolls, that is, a pressure bonded product in which one of resin films is delaminated, and plural administrable agent layers 92 are retained on a surface of a remaining resin film 91 is continuously unwound and fed to a punching device 101. The punching device 101 includes a cutting blade roll 102 and an anvil roll 103. The cutting blade roll is provided with circular cutting blades 102a, for example, with a diameter of 15 mm protruding from a roll outer peripheral surface that rotates. The pressure bonded product is continuously inserted into a nip between the rolls 102 and 103, and when the pressure bonded product stops with the product being sandwiched between the rolls 102 and 103, the administrable agent layers 92 only are punched out by moving the cutting blades 102a protruding from the cutting blade roll 102 so as not to reach a back surface of the resin film 91. A cutting depth by the cutting blade 102a can be controlled by adjusting a clearance between the cutting blade roll 102 and the anvil roll 103. In FIG. 15, the cutting blade roll 102 and the anvil roll 103 are shown as being spaced apart for the sake of clarity, but an actual cutting operation is performed with the cutting blade roll 102 being placed in a position shown by a chain line. In the state where the administrable agent layers only are punched out by the cutting blades 102a, circular cuts 92a corresponding to the shapes of the cutting blades are merely formed in the administrable agent layers 92, and the administrable agent layers 92 remain on the surface of the resin film 91. In this state, the resin film and the administrable agent layers rotate with the rotation of the anvil roll 103, and when they move to a position where suction pads 104 are disposed, the suction pads 104 move toward the anvil roll 103 to suck the administrable agent layers 92 surrounded by the circular cuts 92a and delaminate the circular administrable agent layers 92 from the resin film 91. The circular administrable agent layers 92 are then dropped onto a conveyer (not shown) and fed to a packaging step. Administrable agent layer chips 92b after the circular administrable agent layers are delaminated are wound up together with the resin film 91 as a chip winding roll 105.

A final product of the administrable agent of laminate film form produced by the administrable agent forming apparatus 90 or 100 is in a state where the resin films are delaminated from both surfaces thereof. Thus, the two resin films joined in the pressure bonding step are both finally delaminated.

However, some final products of the administrable agent of laminate film form are of such a type that plural administrable agent layers with a predetermined dimension adhere to a surface of a resin film, and a person who takes the agent delaminates the administrable agent layers from the resin film. For such a final product type, only one of the two resin films joined in the pressure bonding step may be delaminated and removed.

The resin film as a base film for retaining the administrable agent layer may be selected from films made of resin such as polyethylene terephthalate, polyethylene naphthalate, copolymer polyester, polyimide, polypropylene, cellulose triacetate, polyvinyl acetate resin, ethylene-vinyl acetate copolymer, polyethylene, polyvinyl chloride, polycarbonate, polypropylene, triacetate, fluorocarbon resin (ETFE, PFA, FEP), etc. In particular, polyethylene terephthalate (PET) may be preferably used.

It is preferable that the resin film to be delaminated by the delamination roll after the pressure bonding by the pressure bonding apparatus of the invention is previously subjected to release treatment by coating at least a surface (a front surface) provided with the administrable agent layer with a hydrophobic substance so that the resin film is easily delaminated from the administrable agent layer. When the resin film retaining the administrable agent layer is wound into a roll to form a rolled film, a resin film surface (a back surface) provided with no administrable agent layer also comes into contact with the administrable agent layer in the rolled state. At this time, if the back surface of the resin film is not easily delaminated from the administrable agent layer, unwinding of the rolled film becomes difficult. For this reason, when the resin film retaining the administrable agent layer is a rolled film, it is preferable that the resin film to be delaminated is previously subjected to release treatment on both the front surface provided with the administrable agent layer and the opposite back surface, while it is preferable that the resin film retaining the administrable agent layer without being delaminated is previously subjected to release treatment at least on the back surface provided with no administrable agent layer.

The hydrophobic substance coated on the resin film in the release treatment includes silicone resin or wax (bees wax) in compliance with standards for food additives, or the resin film may be coated with metal foil such as aluminum foil or tin foil.

The above description of the invention has been made taken as an example of a batch type operation in which the resin films each retaining the single or the plurality of administrable agent layer/layers are once wound into the rolls to form the rolled film, and then the resin rolled films are pressure bonded. However, the invention may be implemented by a continuous operation in which a plurality of coating apparatus are used and administrable agent layer-formed resin films obtained by the coating apparatus are pressure bonded without being formed into rolled films, or the resin film retaining the plurality of administrable agent layers thus obtained is pressure bonded, without being formed into a rolled film, with another resin film provided with a single or a plurality of administrable agent layer/layers.

Figure 16:
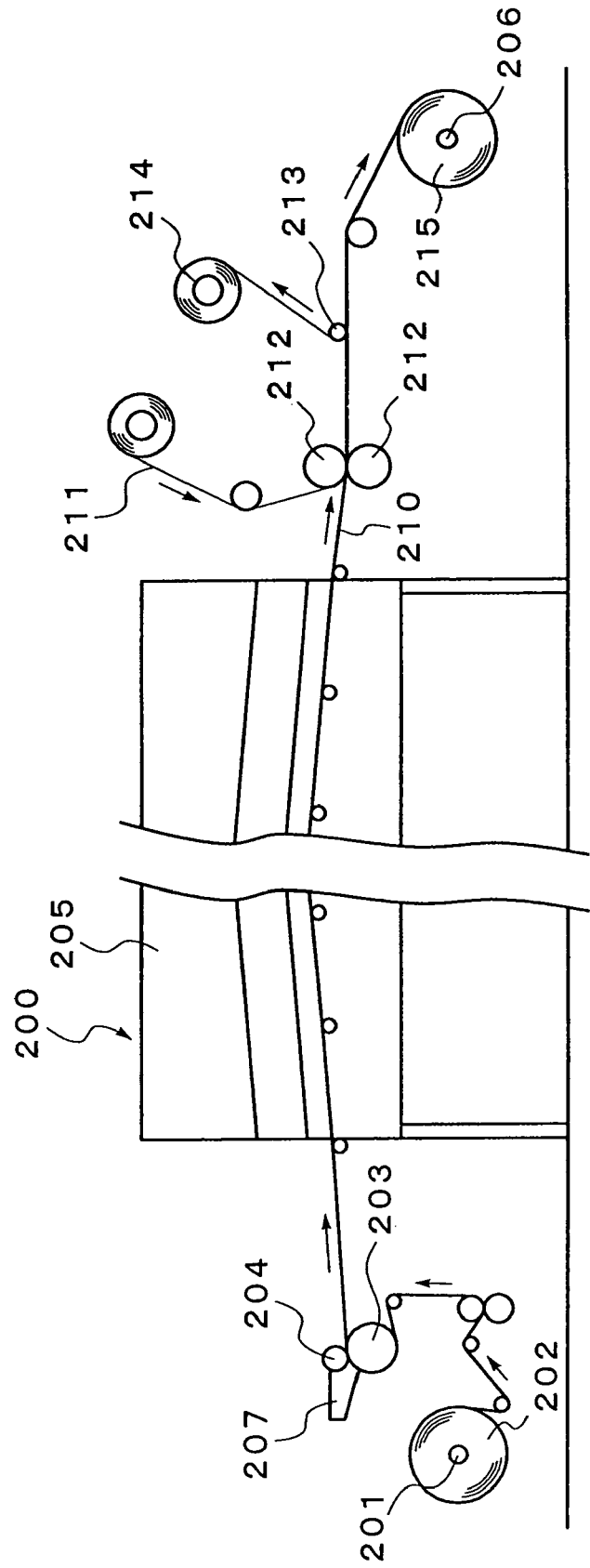
FIG. 16 illustrates another embodiment of a pressure bonding apparatus according to the invention.

In the embodiment in FIG. 1, the administrable agent layer-formed resin film 210 obtained by the coating apparatus 200 is once wound into the roll on the winding roll 206 to form the rolled film, and then the resin film 210 is pressure bonded with another administrable agent layer-formed resin film 210 by the pressure bonding apparatus 10 in FIG. 2. As shown in FIG. 16, however, the administrable agent layer-formed resin film 210 and another administrable agent layer-formed resin film 211 may be directly pressure bonded near an exit of the drying oven 205 before the administrable agent layer-formed resin film 210 fed from the drying oven 205 of the coating apparatus 200 is wound into the roll. Specifically, the two administrable agent layer-formed resin films 210 and 211 are joined together so that the administrable agent layer surfaces face each other, passed through a pair of press rolls 212 and 212 disposed near the exit of the drying oven 205 of the coating apparatus, and pressurized at back surfaces, thereby directly obtaining an intermediate pressure bonded product. The intermediate pressure bonded product is passed through a delamination roll 213 to delaminate an upper resin film, the delaminated resin film is wound up on a winding shaft 214 and continuously delaminated, and then wound up on the winding roll 206 into a roll, thereby forming a plural administrable agent layers-retained rolled film 215, that is, the rolled film retaining the orally administrable edible agent of laminate film form according to the invention.

The laminated structure of the orally administrable agent of laminate film form produced by the method of the invention is not limited, and any number of layers of various types suitable for developing a desired drug effect or function may be laminated. A laminated structure of a general orally administrable agent of film form comprises a covering layer that forms an outermost layer, a drug layer that contains a base and an active ingredient of the administrable agent, and if required, a support layer laminated in succession. The term "edible" herein means that the agent consists of only substances accepted as food and food additives and/or drugs and pharmaceutical additives approved for oral administration, and the term "orally administrable edible agent layer" or the simple term "administrable agent layer" in abbreviated form is used as the term generally referring to an edible covering layer, an edible drug layer, an edible support layer and the like.

The edible covering layer provides a function of protecting a surface of the orally administrable agent of film form or a function of adhering to oral mucosa when used as a patch, and the following substances may be used alone or in combination:

polyvinylpyrrolidone, gelatin, polyvinyl alcohol, sodium polyacrylate, starch, xanthan gum, karaya gum, hydroxypropyl cellulose, water-insoluble methacrylic acid copolymer, ethyl methacrylate and trimethyl ammonium ethyl chloride methacrylate copolymer, dimethylaminoethyl methacrylate and methyl methacrylate copolymer, carboxyvinyl polymer (trade name: Carbopol), tragacanth, gum arabic, locust beans gum, guar gum, dextrin, dextran, amylose, pullulan, chitosan, casein, alkyl ester alginate, or the like.

As the base used with the effective ingredient in the edible drug layer, the following substances may be used alone or in combination:

polyvinylpyrrolidone, polyvinyl alcohol, sodium polyacrylate, carboxymethyl cellulose, starch, xanthan gum, karaya gum, sodium alginate, methylcellulose, carboxyvinyl polymer, agar, hydroxypropyl cellulose, hydroxypropylmethylcellulose phthalate (HPMCP), cellulose acetate phthalate (CAP), carboxymethylethylcellulose (CMEC), ethylcellulose, hydroxyethylcellulose, hydroxypropylmethylcellulose, carboxyvinyl polymer (trade name: Carbopol), tragacanth, gum arabic, locust beans gum, guar gum, carrageenan, dextrin, dextran, amylose, carboxymethyl cellulose potassium, carboxymethyl cellulose sodium, carboxymethyl cellulose calcium, pullulan, chitosan, starch, polyvinyl alcohol, carboxymethylethylcellulose, carboxymethyl starch, seed coat of plantago, galactomannan, eudragit, casein, alkyl ester alginate, or the like.

The edible support layer is for preventing elution of the effective ingredient to a non-target site in oral cavity, and an object may be achieved by using the following substances alone or in combination to form a difficultly soluble layer or an insoluble layer in the oral cavity:

gelatin, carboxymethyl cellulose, methylcellulose, carboxyvinyl polymer, agar, hydroxypropyl cellulose, hydroxypropylmethylcellulose phthalate (HPMCP), cellulose acetate phthalate (CAP), carboxymethylethylcellulose (CMEC), ethylcellulose, hydroxyethylcellulose, hydroxypropylmethylcellulose, cellulose acetate phthalate, locust beans gum, guar gum, carrageenan, carboxymethyl cellulose potassium, carboxymethyl cellulose sodium, carboxymethyl cellulose calcium, shellac resin (shellac, white clear shellac), starch, cellulose acetate, polyvinyl alcohol, hydroxyethylmethylcellulose, carboxymethyl starch, seed coat of plantago, galactomannan, eudragit, or the like.

The orally administrable agent of laminate film form produced by the method of the invention preferably contains at least one substance having a thermoplastic property among the edible substances described above in each of the administrable agent layers (the edible covering layer, drug layer, support layer, or the like) bonded together. The administrable agent layers containing the thermoplastic substance are slightly softened by heating and reliably bonded together. As the edible substance having a remarkable thermoplastic property, the following substances may be used, and each of the administrable agent layers bonded together preferably contains the edible thermoplastic substance selected from the following substances alone or in combination:

amylose, carboxymethyl cellulose potassium, carboxymethyl cellulose sodium, carboxymethyl cellulose calcium, alkyl ester alginate, sodium alginate, ethylcellulose, eudragit, carboxymethylethylcellulose, carboxymethyl starch, carboxymethyl cellulose, agar, gelatin, shellac, dextran, dextrin, starch, tragacanth, hydroxyethylcellulose, hydroxypropylcellulose, hydroxypropylmethylcellulose, hydroxypropylmethylcellulose phthalate, polyvinylpyrrolidone, methacrylic acid copolymer, methylcellulose phthalate, or the like.

In the orally administrable agent of laminate film form according to the invention, the following drugs may be used as the effective ingredient contained in the edible drug layer:

central nervous system drugs (hypnotic sedative drugs, antianxiety drugs, antiepileptic drugs, antipyretic, analgesic and antiphlogistic drugs, analeptic drugs, stimulant drugs, antiparkinson drugs, psychoneurotic drugs, combination cold remedies, or the like), peripheral nervous system drugs (local anesthetics, skeletal muscle relaxants, autonomic drugs, antispasmodic drugs, or the like), sensory organ drugs (ophthalmic drugs, antidinic drugs, or the like), circulatory organ drugs (cardiac stimulants, antiarrhythmic drugs, diuretics, antihypertensive drugs, vasoconstrictors, vasodilators, antihyperlipidemic drugs, or the like), respiratory organ drugs (respiratory stimulants, antitussive drugs, expectorants, bronchodilators, mouthrinses, or the like), digestive organ drugs (emetocathartics, intestinal remedies, peptic ulcer drugs, cathartics, enemas, or the like), hormone drugs (salivary gland hormone drugs, thyroid gland and parathyroid gland hormone drugs, protein anabolic steroids, adrenal gland hormone drugs, follicular and corpus luteum hormone drugs, mixed hormone drugs, or the like), urogenital organ and anus drugs (uterotonic drugs, contraceptive drugs, hemorrhoid drugs, or the like), dermatologic drugs (methoxsalen or the like), dental and oral cavity drugs (dental antibiotic preparations or the like), vitamin preparations, analeptics (mineral preparations), blood and body fluid drugs (anticoagulant or the like), liver disease drugs, antidotes, antipodagrics, diabetic drugs, cell activators, antitumor drugs (alkylating agents, antimetabolites, or the like), antiallergic drugs (antihistamines or the like), crude drugs, herbal preparations, antibiotic preparations, antiviral drugs, anthelmintics, alkaloid narcotics (opium alkaloid preparations, coca alkaloid preparations, or the like), and non-alkaloid narcotics (synthetic narcotics such as fentanyl citrate), or the like.

As the effective ingredient contained in the drug layer, orally administrable agents may be used of quasi drugs, cosmetics and health food having a deodorizing effect or a health-maintaining effect.

The edible covering layer, drug layer, and support layer that are the administrable agent layers of the orally administrable agent of laminate film form produced by the method of the invention may be obtained by using the above described ingredient dissolved or dispersed in the following solvent to perform coating and drying in the administrable agent layer forming step:

water, ethanol, acetic acid, acetone, anisole, 1-butanol, 2-butanol, n-butyl acetate, t-butylmethylether, cumene, dimethylsulfoxide, ethyl acetate, diethyl ether, ethyl formate, formic acid, heptane, isobutyl acetate, isopropyl acetate, methyl acetate, 3-methyl-1-butanol, methyl ethyl ketone, methyl isobutyl keton, 2-methyl-1-propanol, pentane, 1-pentanol, 1-propanol, 2-propanol, propyl acetate, tetrahydrofuran, acetonitrile, chlorobenzene, chloroform, cyclohexane, 1,2-dichloroethene, dichloromethane, 1,2-dimethoxyethane, N,N-dimethylacetamide, N,N-dimethylformamide, 1,4-dioxane, 2-ethoxyethanol, ethylene glycol, formamide, hexane, methanol, 2-methoxyethanol, methyl butyl ketone, methylcyclohexane, N-methylpyrrolidone, nitromethane, pyridine, sulfolane, tetralin, toluene, 1,1,2-trichloroethene, xylene, 1,1-diethoxypropane, 1,1-dimethoxymethane, 2,2-dimethoxypropane, isooctane, isopropyl ether, methylisopropylketon, methyltetrahydrofuran, petroleum ether, trichloroacetic acid, trifluoroacetic acid, methylene chloride, or the like. Among these solvents, ethanol, water, ethyl acetate or a combination thereof (for example, ethanol-water mixture, ethanol-ethyl acetate mixture) is most preferably used.

To each administrable agent layer of the orally administrable agent of laminate film form produced by the method of the invention, edible additives may be added, if required, such as plasticizers, for example, polyethylene glycol (Macrogol), glycerine, propylene glycol or the like, taste corrigents, flavor corrigents, or coloring agents. As the taste corrigents, sweeteners such as saccharin, glycyrrhizinic acid, sucrose, fructose or mannitol, refrigerants such as menthol or peppermint oil, and organic acid compounds that provide acid taste such as citrate, tartaric acid or fumarate, can be used. As the flavor corrigents, natural or synthetic flavor can be used. As the coloring agents, agents used in general preparations such as edible lake may be used.

Examples

Now, an example of producing a troche of film form will be described as a method for producing an orally administrable edible agent of laminate film form having a multilayer structure including laminated extremely thin orally administrable edible agent layers according to the invention, but the invention is not limited thereto.

<Preparation of Covering Layer Preparation Solution>

To an appropriate amount of purified water, 20.0 parts by weight of pulluran and 5.0 parts by weight of D-sorbitol were added and dissolved while stirring to obtain an edible covering layer preparation solution.

<Preparation of Drug Layer I Preparation Solution>

To an appropriate amount of ethanol, 1.5 parts by weight of cetylpyridinium chloride, 1.5 parts by weight of chlorpheniramine maleate, 4.5 parts by weight of Macrogol 400, 2.5 parts by weight of l-menthol, 22.5 parts by weight of polyvinyl pyrrolidone K90, and 59.0 parts by weight of hydroxypropylcellulose were added and dissolved while stirring. Then, to the resulting solution, 3.8 parts by weight of dipotassium glycyrrhizinate and 0.5 part by weight of saccharin sodium added to an appropriate amount of purified water was added and further mixed while stirring to obtain an edible drug layer I preparation solution.

<Preparation of Drug Layer II Preparation Solution>

To an appropriate amount of ethanol, 4.5 parts by weight of cetylpyridinium chloride, 4.5 parts by weight of chlorpheniramine maleate, 7.0 parts by weight of tannic acid, 13.5 parts by weight of Macrogol 400, 7.5 parts by weight of l-menthol, 67.5 parts by weight of polyvinyl pyrrolidone K90, and 182.0 parts by weight of hydroxypropylcellulose were added and dissolved while stirring. Then, to the resulting solution, 11.2 parts by weight of dipotassium glycyrrhizinate and 1.5 parts by weight of saccharin sodium added to an appropriate amount of purified water was added and further mixed while stirring to obtain an edible drug layer II preparation solution.

<Administrable Agent Layer Forming Step>

(1) Application of Covering Layer and Drug Layer I (1)-1: Forming of Covering Layer On the unwinding roll 201 of the coating apparatus 200 in FIG. 1, a polyethylene terephthalate (PET) film whose back surface was subjected to silicone release treatment was set, and the covering layer preparation solution was supplied to the dam portion 207 to apply the edible covering layer preparation solution on a front surface (a surface that is not subjected to the silicone release treatment) of the polyethylene terephthalate film. At this time, a clearance between the doctor roll 204 and the polyethylene terephthalate film was set at 30 μm, a coating amount at 30 g/m$^2$, and a drying temperature in the drying oven 205 at 60° C., and the polyethylene terephthalate film of 200 m+α (corresponding to a length of loss) provided with a covering layer of 8 to 12 μm thick was wound up on the winding roll 206 into a roll.

(1)-2: Application of Drug Layer I on Covering Layer

Figure 17A:
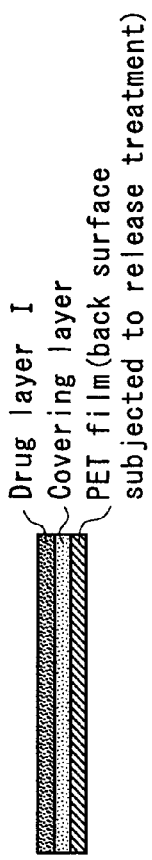
FIGS. 17(A) to 17(E) are sectional views illustrating laminated structures obtained by the embodiment of the invention.

The polyethylene terephthalate film provided with the covering layer, which was obtained in (1)-1 and wound into the roll, was set on the unwinding roll 201 of the coating apparatus 200 in FIG. 1, and the drug layer I preparation solution was supplied to the dam portion 207 to apply the edible drug layer I preparation solution on the covering layer. At this time, a clearance between the doctor roll 204 and the polyethylene terephthalate film was set at 500 μm, and a coating amount at 280 g/m$^2$, and the polyethylene terephthalate film of approximately 200 m provided with a drug layer I of 55 to 75 μm thick was wound up on the winding roll 206 into a roll. A laminated structure of an intermediate product A thus obtained is shown in FIG. 17(A).

(2) Application of Drug Layer II

Figure 17B:
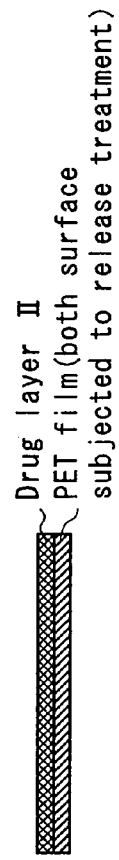

On the unwinding roll 201 of the coating apparatus 200 in FIG. 1, a polyethylene terephthalate film whose both surfaces, were subjected to silicone release treatment was set, and the drug layer II preparation solution was supplied to the dam portion 207 to apply the edible drug layer II preparation solution on a front surface of the polyethylene terephthalate film. At this time, a clearance between the doctor roll 204 and the polyethylene terephthalate film was set at 550 μm, and a coating amount at 320 g/m$^2$, and the polyethylene terephthalate film of 400 m+β (corresponding to a length of loss) provided with the drug layer II of 55 to 75 μm thick was wound up on the winding roll 206 into a roll. A laminated structure of an intermediate product B thus obtained is shown in FIG. 17(B).

<Administrable Agent Layers Bonding Step>

(1) First Step

The intermediate product B (approximately 400 m) wound in the roll was set on the upper unwinding roll 18 of the pressure bonding apparatus 10 in FIG. 2, and the intermediate product A (approximately 200 m) wound in the roll was set on the lower unwinding roll 20. An administrable agent layer of the intermediate product A and an administrable agent layer of the intermediate product B that were unwound were introduced into the nip between the pair of press rolls 11 and 11 so that they face each other, and the administrable agent layers were bonded together at a pressure bonding temperature of 65° C. and a pressure of 0.3 MPa and laminated.

Figure 17C:
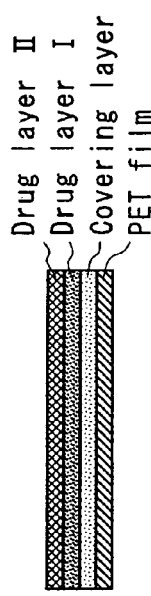

The polyethylene terephthalate film of the intermediate product B only located in an upper surface of an intermediate pressure bonded product after passing through the press rolls 11 and 11 was drawn along the peripheral surface of the delamination roll 13, wound up on the delamination film winding shaft 14 and delaminated from a laminated product, and then the intermediate pressure bonded product was wound up on the winding roll 15 into a roll. The temperature of the intermediate pressure bonded product when the polyethylene terephthalate film was delaminated was 50° C. by natural heat dissipation. A laminated structure of an intermediate product C (approximately 200 m) thus obtained is shown in FIG. 17(C).

When the first step is finished, 200 m among approximately 400 m of the intermediate product B remains on the upper unwinding roll 18, and the entire intermediate product A of approximately 200 m is unwound from the lower unwinding roll 20.

(2) Second Step

After the first step was finished, the obtained intermediate product C (approximately 200 m) wound into the roll was set on the lower unwinding roll 20 of the pressure bonding apparatus 10 in FIG. 2. The remainder of the intermediate product B of approximately 200 m wound into the roll was set on the upper unwinding roll 18.

In this state, the administrable agent layer of the intermediate product B and the administrable agent layer of the intermediate product C that were unwound were introduced into the nip between the pair of press rolls 11 and 11 so that they face each other, and the administrable agent layers were bonded together at the same temperature and pressure as in the first step and laminated.

Figure 17D:
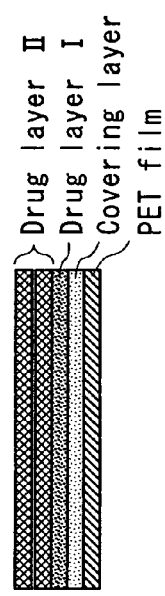

The polyethylene terephthalate film of the intermediate product B only located in an upper surface of an intermediate pressure bonded product after passing through the press rolls 11 and 11 was drawn along the peripheral surface of the delamination roll 13, wound up on the delamination film winding shaft 14 and delaminated from the intermediate pressure bonded product, and then the intermediate pressure bonded product was wound up on the winding roll 15 into a roll. The temperature of the intermediate pressure bonded product in delamination was also the same as in the first step. The intermediate pressure bonded product thus obtained was wound up on separate rolls for each 100 m to obtain an intermediate product D (100 m) and an intermediate product D' (100 m). The intermediate products D and D' have completely the same laminated structure as shown in FIG. 17(D).

(3) Third Step

The intermediate product D (100 m) and the intermediate product D' (100 m) having the same structure and wound into the rolls, which were obtained in the second step described above, were set on the upper unwinding roll 18 and the lower unwinding roll 20, respectively, of the pressure bonding apparatus 10 as shown in FIG. 6. An administrable agent layer of the intermediate product D and an administrable agent layer of the intermediate product D' that were unwound were introduced into the nip between the pair of press rolls 11 and 11 so that they face each other, and the administrable agent layers were bonded together at the same temperature and pressure as in the first step and laminated.

Figure 17E:
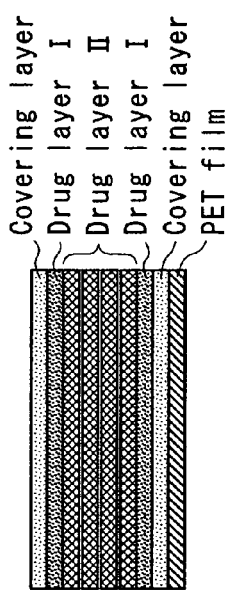

The polyethylene terephthalate film of the intermediate product D only located in an upper surface of an intermediate pressure bonded product after passing through the press rolls 11 and 11 was drawn along the peripheral surface of the delamination roll 13, and wound up on the delamination film winding shaft 14 and delaminated from the intermediate pressure bonded product. Then, the intermediate pressure bonded product is passed through the slitter 30 in contact with the roll 16 and cut, and the cut narrow intermediate pressure bonded products were alternately wound up on the winding reels 33a set on the shaft 34a and the winding reels 33b set on the shaft 34b. The temperature of the intermediate pressure bonded product in delamination was also the same as in the first step. A laminated structure of an intermediate product E thus obtained is shown in FIG. 17(E).

<Administrable Agent Punching Step>

A circular troche of film form was obtained by a method of using the administrable agent forming apparatus 100 in FIG. 15 to punch out the laminated administrable agent layer only from the edible administrable agent of laminate film form that is the laminated product of film form obtained as the intermediate product E, with the circular cutting blade 102a having the diameter of 15 mm, so as not to reach the back surface of the polyethylene terephthalate film, or a method of delaminating the polyethylene terephthalate film on the back surface from the laminated product of film form obtained as the intermediate product E to obtain the laminated administrable agent layer only, and then using the administrable agent forming apparatus 90 in FIG. 14 to punch out the laminated administrable agent layer with the circular cutting blade 94a.

Figure 18:
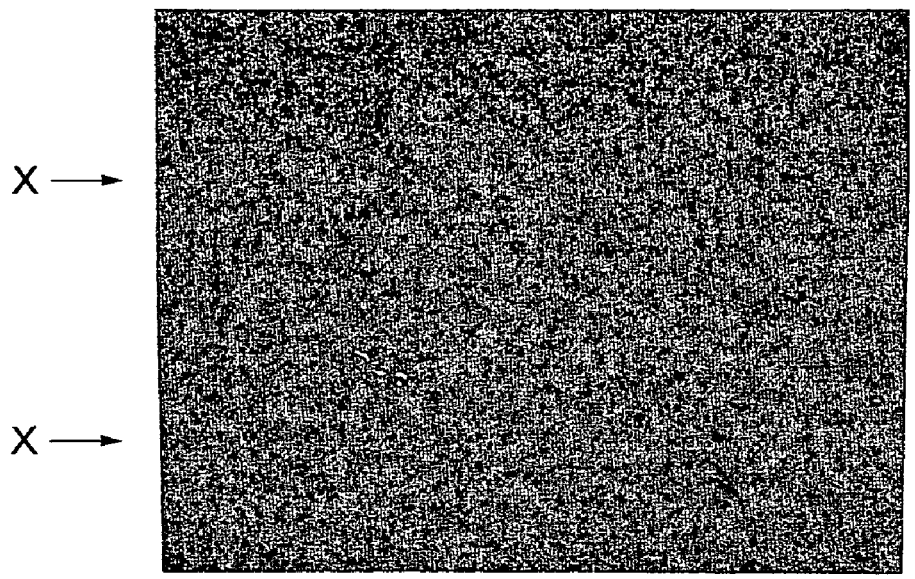
FIG. 18 is a photomicrograph (×800) showing a section of the final pressure bonded product obtained by the invention and a similar laminated product obtained by a conventional lamination coating technique.
Figure 18:
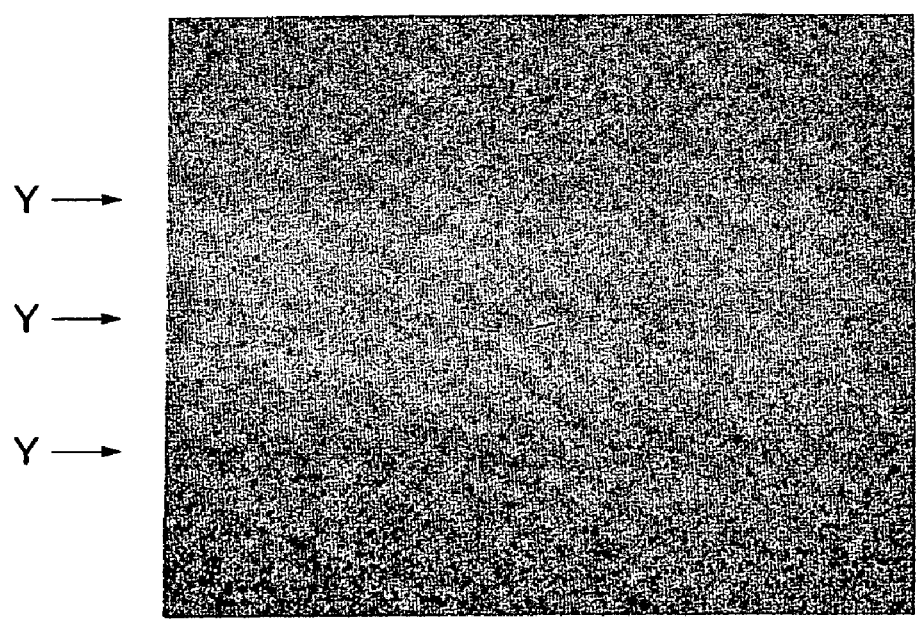

A photomicrograph showing a section of the troche of film form thus obtained, which was observed using "Digital microscope BS-D8000II" (trade name, produced by Sonic Co., LTD), is shown as "technique of the invention" in FIG. 18. For comparison, a section, which was similarly observed, of a conventional laminated product of film form having similar laminated administrable agent layers obtained using the coating apparatus 200 in FIG. 1 is shown as "lamination coating technique" in FIG. 18. In the section obtained by the method according to the invention, boundaries X and X between the administrable agent layers appear clear and the laminated administrable agent layers can be definitely identified. On the other hand, in the section obtained by the conventional "lamination coating technique", boundaries Y and Y between the administrable agent layers appear unclear and blurred, and the laminated administrable agent layers cannot be identified. This is because when the administrable agent layer preparation solution is applied in a laminated manner on the lower administrable agent layer applied and dried, the solvent in the administrable agent layer preparation solution applied thereon permeates the lower administrable agent layer and is welded by solvent welding.

When the solvent in the administrable agent layer preparation solution applied in the laminated manner permeates the lower administrable agent layer, the effective ingredient in the preparation solution may also move to the lower administrable agent layer together with the solvent. This may cause trouble in causing each administrable agent layer to contain the same effective ingredient with different concentration. Specifically, even if the content of the effective ingredient in each administrable agent layer preparation solution applied in the laminated manner is adjusted so that an outer side of the laminated structure contains the effective ingredient with low concentration and an inner side of the laminated structure contains the effective ingredient with high concentration, movement of the effective ingredient resulting from the permeation of the solvent at the boundary surfaces prevents accurate control of the concentration of the effective ingredient in each administrable agent layer. On the other hand, in the laminated structure by the pressure bonding method according to the invention, the administrable agent layers are definitely identified at the boundary surfaces, thereby preventing permeation of the solvent and resulting movement of the effective ingredient, and allowing accurate control of the concentration of the effective ingredient in each administrable agent layer.

INDUSTRIAL APPLICABILITY

As is apparent from the above detailed description, according to the method for producing the orally administrable edible agent of laminate film form using the pressure bonding technique according to the invention, the orally administrable edible agent of laminate film form can be obtained having the multilayer structure including laminated extremely thin layers with high productivity that can improve quantitative accuracy required for pharmaceutical preparations, and prevents time constraint in the drying step or the like, as compared with the conventional lamination coating technique of repeating coating and drying of the orally administrable edible agent layer preparation solution to form the multilayer structure.

Further, in the laminated structure obtained by the conventional lamination coating technique, the boundary between the laminated orally administrable edible agent layers appears unclear and blurred. On the other hand, in the laminated structure obtained by the method of the invention, the boundary between the orally administrable edible agent layers can be definitely identified, and such a laminated structure is a novel structure of the orally administrable edible agent of laminate film form obtained first by the invention. The boundary between the laminated orally administrable edible agent layers can be definitely identified, which means the orally administrable edible agent layers are definitely divided without being mixed near the boundary. This allows accurate control of the concentration of the effective ingredient in each orally administrable edible agent layer.

According to the orally administrable edible agent of laminate film form of the invention, the orally administrable edible agent of film form has strength sufficient to form the self-supporting film to cause the orally administrable edible agent layers to adhere to one resin film to be delaminated, which tends to cause trouble that the orally administrable edible agent layers cannot be retained on the other (another) intended resin film. However, the orally administrable agent layers can be reliably retained on the other intended resin film by conveying the two resin films sandwiching the bonded orally administrable edible agent layers in the direction substantially conforming to the tangential direction at the pressurization zone of the pair of press rolls, and drawing one of the two resin films sandwiching the bonded orally administrable edible agent layers in the direction different from the conveying direction along the peripheral surface of the delamination roll disposed in the conveying direction, while continuously conveying the other resin film retaining the orally administrable edible agent layers in the conveying direction, thereby providing the method for producing an orally administrable edible agent of laminate film form with high productivity.

Further, according to the pressure bonding apparatus of the invention, the orally administrable edible agent of film form has strength sufficient to form the self-supporting film as described above, which tends to cause trouble that the orally administrable edible agent layers to adhere to one resin film to be delaminated. However, the delamination roll is disposed in the position along the conveying direction of the resin film conveyed from the pair of press rolls, the delamination roll has the small diameter of 6 cm or less, and one resin film to be delaminated only is drawn and delaminated in the direction different from the conveying direction of the other resin film, thereby allowing the orally administrable edible agent layer to be reliably retained on the other intended resin film to provide the pressure bonding apparatus with high productivity.

The delamination roll may be rotated with movement of one resin film to be delaminated, or the winding shaft may be disposed in the position where one resin film to be delaminated only is drawn at the angle of 45° or more to the conveying direction of the other resin film with the delamination roll as the starting point, thereby allowing smooth and reliable delamination of the resin film to be delaminated.

The pair of unwinding rolls that feed the two resin films each provided with the orally administrable edible agent layer and the winding roll that winds up the intermediate pressure bonded product may have substantially the same dimension and structure and be interchangeable. Thus, the intermediate pressure bonded product is once wound up on the winding roll to form the rolled film, and the resulting rolled film is set again as it is in the position of the winding roll as a starting material of the pressure bonding apparatus, thereby allowing the orally administrable edible agent of film form having the multilayer structure to be easily formed in the batch manner.

In individually winding up each of the pressure bonded products cut and divided into the plurality of pieces by the slitter on the winding reel corresponding to each of the pressure bonded products, the winding shafts of the winding reels are staggered backward and forward without gaps, and there is no need for providing spaces between the narrow pressure bonded products cut and divided into the plurality of pieces. This allows the pressure bonded products cut and divided into the narrow strips to be individually and smoothly wound up on the winding reel without causing distortion, wrinkles or cracks in the orally administrable agent layers retained on the pressure bonded product.

The shaft that supports the winding reel that individually winds up the plurality of narrow pressure bonded products film by operating the slitter and the winding roll that winds up the intermediate pressure bonded product are interchangeable. This allows easy switching as required between the cutting and dividing operation of the pressure bonded product by the slitter, and the pressure bonding operation in the batch manner without the slitter being operated, thereby providing the pressure bonding apparatus of an orally administrable edible agent of film form that is generally compact and requires a small installation area.

Further, the shaft that supports the plurality of winding reels is supported at both ends thereof by frames, one end of the shaft is cantilevered by one of the frames, and the other frame that supports the other end of the cantilevered shaft can be brought up and down. This allows the winding reels supported by the shaft to be easily and quickly mounted to or removed from the shaft with the shaft being cantilevered, and eliminates the need for moving the entire shaft that supports the plurality of winding reels, thereby extremely improving workability.

Each of the winding reels is rotatably supported by the shaft, the side wall of each winding reel is pressed by the spring disposed at one end of the shaft and urged toward the other end of the shaft, and an urging force of the spring that presses the winding reel side wall causes rotation of the shaft to be transmitted to the winding reel. Thus, adjusting the urging force of the spring allows the degree of slip of the winding reel with respect to the shaft to be adjusted. Therefore, the winding force can be easily controlled depending on the variation of the winding amount of the resin film on the winding reel, thereby eliminating the need for installing the expensive control device.

The invention claimed is:

1. A method for producing an orally administrable edible agent of laminate film form, the method comprising:
forming a plurality of orally administrable edible agent layers, wherein each orally administrable edible agent layer has a predetermined thickness and is formed on a surface of a respective resin film by coating and drying;
joining together two orally administrable edible agent layers so that orally administrable edible agent layer surfaces face each other and the orally administrable edible agent layers are sandwiched between the resin films of the two orally administrable edible agent layers, and pressurizing the resin films at back surfaces by a pair of press rolls so as to bond the orally administrable edible agent layers together such that ingredients of each of the orally administrable edible agent layers do not permeate the other of the orally administrable edible agent layers, wherein the orally administrable edible agent layers include the same ingredients or different ingredients; and delaminating only one of the two resin films by conveying the two resin films sandwiching the bonded orally administrable edible agent layers in a substantially tangential direction at a pressurization zone of the pair of press rolls, and drawing only one of the two resin films sandwiching the bonded orally administrable edible agent layers in a direction different from the conveying direction along a peripheral surface of a delamination roll disposed in the conveying direction while continuously conveying the other resin film retaining the bonded orally administrable edible agent layers in the conveying direction.

2. The method for producing an orally administrable edible agent of laminate film form according to claim 1, wherein the one resin film to be delaminated in said delaminating of only one of the two resin films is previously subjected to release treatment at least on a surface provided with the orally administrable edible agent layer.

3. The method for producing an orally administrable edible agent of laminate film form according to claim 1, wherein said pressurizing of the resin films at back surfaces by the pair of press rolls comprises pressurizing the resin films at a pressure of 0.05 to 1.5 MPa.

4. The method for producing an orally administrable edible agent of laminate film form according to claim 1, wherein a temperature of the orally administrable edible agent layers is 50° C. to 180° C. during said joining together of the two orally administrable edible agent layers.

5. The method for producing an orally administrable edible agent of laminate film form according to claim 4, further comprising:

cooling the bonded orally administrable edible agent layers to a temperature at least 10° C. lower than the temperature of the orally administrable edible agent layers during said joining together of the two orally administrable edible agent layers, and such that the temperature of the cooled orally administrable edible agent layers is higher than 0° C., wherein said cooling of the bonded orally administrable edible agent layers occurs after said joining together of the two orally administrable edible agent layers and before said delaminating of only one of the two resin films.

6. The method for producing an orally administrable edible agent of laminate film form according to claim 4, wherein each of the bonded orally administrable edible agent layers includes an edible thermoplastic substance.

7. The method for producing an orally administrable edible agent of laminate film form according to claim 6, wherein the edible thermoplastic substance includes at least one selected from the group consisting of amylose, carboxymethyl cellulose potassium, carboxymethyl cellulose sodium, carboxymethyl cellulose calcium, alkyl ester alginate, sodium alginate, ethylcellulose, eudragit, carboxymethylethylcellulose, carboxymethyl starch, carboxymethyl cellulose, agar, gelatin, shellac, dextran, dextrin, starch, tragacanth, hydroxyethylcellulose, hydroxypropylcellulose, hydroxypropylmethylcellulose, hydroxypropylmethylcellulose phthalate, polyvinylpyrrolidone, methacrylic acid copolymer, and methylcellulose phthalate.

8. The method for producing an orally administrable edible agent of laminate film form according to claim 1, wherein a thickness of each of the bonded orally administrable edible agent layers is 1 to 300 µm.

9. The method for producing an orally administrable edible agent of laminate film form according to claim 1, wherein the bonded orally administrable edible agent layers are self-supporting laminated films.

10. The method for producing an orally administrable edible agent of laminate film form according to claim 9, further comprising:

delaminating the other resin film retaining the orally administrable edible agent layers so as to finally delaminate the resin films from the bonded orally administrable edible agent layers.

11. A method for producing an orally administrable edible agent of laminate film form, comprising:

forming a plurality of orally administrable edible agent layers, wherein each orally administrable edible agent layer has a predetermined thickness and is formed on a surface of a respective resin film by coating and drying;

joining together first and second orally administrable edible agent layers so that orally administrable edible agent layer surfaces face each other and the orally administrable edible agent layers are sandwiched between corresponding first and second resin films of the first and second orally administrable edible agent layers, and pressurizing the resin films at back surfaces by a pair of press rolls so as to bond the orally administrable edible agent layers together such that ingredients of each of the first and second orally administrable edible agent layers do not permeate the other of the first and second orally administrable edible agent layers, wherein the orally administrable edible agent layers include the same ingredients or different ingredients;

delaminating only one of the first and second resin films by conveying the first and second resin films sandwiching the bonded orally administrable edible agent layers in a substantially tangential direction at a pressurization zone of the pair of press rolls, and drawing only one of the first and second resin films sandwiching the bonded orally administrable edible agent layers in a direction different from the conveying direction along a peripheral surface of a delamination roll disposed in the conveying direction while continuously conveying the other of the first and second resin films retaining the bonded orally administrable edible agent layers in the conveying direction;

joining together a third orally administrable edible agent layer and the bonded first and second orally administrable edible agent layers so that orally administrable edible agent layer surfaces face each other and the first, second and third orally administrable edible agent layers are sandwiched between a corresponding third resin film of the third orally administrable edible agent layer and the other of the first and second resin films retaining the bonded first and second orally administrable edible agent layers, and pressurizing the resin films at back surfaces by the pair of press rolls so as to bond the first, second and third orally administrable edible agent layers together such that ingredients of each of the orally administrable edible agent layers do not permeate any other of the orally administrable edible agent layers, wherein the third orally administrable edible agent layer includes the same ingest ingredients or different ingredients as that of the bonded first and second orally administrable edible agent layers; and delaminating only one of the resin films sandwiching the bonded first, second and third orally administrable edible agent layers by conveying the resin films sandwiching the bonded first, second and third orally administrable edible agent layers in the substantially tangential direction at the pressurization zone of the pair of press rolls, and drawing only one of the resin films sandwiching the bonded first, second and third orally administrable edible agent layers in a direction different from the conveying direction along the peripheral surface of the delamination roll disposed in the conveying direction while continuously conveying the other of the resin films retaining the first, second and third orally administrable edible agent layers in the conveying direction.

12. The method for producing an orally administrable edible agent of laminate film form according to claim 11, wherein the one resin film to be delaminated in said delaminating of only one of the first and second resin films is previously subjected to release treatment at least on a surface provided with the orally administrable edible agent layer.

13. The method for producing an orally administrable edible agent of laminate film form according to claim 11, wherein the one resin film to be delaminated in said delaminating of only one of the resin films sandwiching the bonded first, second and third orally administrable edible agent layers is previously subjected to release treatment at least on a surface provided with the orally administrable edible agent layer.

14. The method for producing an orally administrable edible agent of laminate film form according to claim 11, wherein said pressurizing of the resin films in said joining together of the first and second orally administrable edible agent layers and in said joining together of the third orally administrable edible agent layer and the bonded first and second orally administrable edible agent layers comprises pressurizing the resin films at a pressure of 0.05 to 1.5 MPa.

15. The method for producing an orally administrable edible agent of laminate film form according to claim 11, wherein a temperature of the orally administrable edible agent layers is 50° C. to 180° C. during said joining together of the first and second orally administrable edible agent layers and during said joining together of the third orally administrable edible agent layer and the bonded first and second orally administrable edible agent layers.

16. The method for producing an orally administrable edible agent of laminate film form according to claim 11, wherein a thickness of each of the bonded first, second and third orally administrable edible agent layers is 1 to 300 μm.

17. The method for producing an orally administrable edible agent of laminate film form according to claim 11, wherein the bonded first, second and third orally administrable edible agent layers are self-supporting laminated films.

18. A method for producing an orally administrable edible agent of laminate film form, comprising:

forming a plurality of orally administrable edible agent layers, wherein each orally administrable edible agent layer has a predetermined thickness and is formed on a surface of a respective resin film by coating and drying;

winding each of the orally administrable edible agent layers into a roll so as to form a plurality of rolled films;

unwinding and joining together two rolled films so that surfaces of the orally administrable edible agent layers of the two rolled films face each other and the orally administrable edible agent layers are sandwiched between the resin films of the two rolled films, and pressurizing the resin films at back surfaces by a pair of press rolls so as to bond the orally administrable edible agent layers together such that ingredients of each of the orally administrable edible agent layers do not permeate the other of the orally administrable edible agent layers, wherein the orally administrable edible agent layers include the same ingredients or different ingredients; and delaminating only one of the two resin films by conveying the two resin films sandwiching the bonded orally administrable edible agent layers in a substantially tangential direction at a pressurization zone of the pair of press rolls, and drawing only one of the two resin films sandwiching the bonded orally administrable edible agent layers in a direction different from the conveying direction along a peripheral surface of a delamination roll disposed in the conveying direction while continuously conveying the other resin film retaining the bonded orally administrable edible agent layers in the conveying direction.

19. The method for producing an orally administrable edible agent of laminate film form according to claim 18, wherein the one resin film to be delaminated in said delaminating of only one of the two resin films is previously subjected to release treatment on both a front surface to provided with the orally administrable edible agent layer and an opposite back surface, and the other resin film on which the bonded orally administrable edible agent layers are to be retained in said delaminating of only one of the two resin films is previously subjected to release treatment at least on a back surface which is not to be provided with an orally administrable edible agent layer.

20. The method for producing an orally administrable edible agent of laminate film form according to claim 18, wherein said pressurizing of the resin films at back surfaces by the pair of press rolls comprises pressurizing the resin films at a pressure of 0.05 to 1.5 MPa.

21. The method for producing an orally administrable edible agent of laminate film form according to claim 18, wherein a temperature of the orally administrable edible agent layers is 50° C. to 180° C. during said joining together of the two rolled films.

22. The method for producing an orally administrable edible agent of laminate film form according to claim 18, wherein a thickness of each of the bonded orally administrable edible agent layers is 1 to 300 μm.

23. The method for producing an orally administrable edible agent of laminate film form according to claim 18, wherein the bonded orally administrable edible agent layers are self-supporting laminated films.

24. A method for producing an orally administrable edible agent of laminate film form, comprising:

forming a plurality of orally administrable edible agent layers, wherein each orally administrable edible agent layer has a predetermined thickness and is formed on a surface of a respective resin film by coating and drying;

winding each of the orally administrable edible agent layers into a roll so as to form a plurality of rolled films;

unwinding and joining together first and second rolled films so that surfaces of corresponding first and second orally administrable edible agent layers of the first and second rolled films face each other and the orally administrable edible agent layers are sandwiched between corresponding first and second resin films of the first and second rolled films, and pressurizing the resin films at back surfaces by a pair of press rolls so as to bond the orally administrable edible agent layers together such that ingredients of each of the first and second orally administrable edible agent layers do not permeate the other of the first and second orally administrable edible agent layers, wherein the orally administrable edible agent layers include the same ingredients or different ingredients;

delaminating only one of the first and second resin films by conveying the first and second resin films sandwiching the bonded orally administrable edible agent layers in a substantially tangential direction at a pressurization zone of the pair of press rolls, and drawing only one of the first and second resin films sandwiching the bonded orally administrable edible agent layers in a direction different from the conveying direction along a peripheral surface of a delamination roll disposed in the conveying direction while continuously conveying the other of the first and second resin films retaining the bonded first and second orally administrable edible agent layers in the conveying direction;

winding the resin film retaining the bonded orally administrable edible agent layers into a roll;

unwinding and joining together a third rolled film and the roll having the bonded first and second orally administrable edible agent layers so that surfaces of a corresponding third orally administrable edible agent layer of the third rolled film and one of the first and second orally administrable edible agent layers face each other and the first, second and third orally administrable edible agent layers are sandwiched between a corresponding third resin film of the third rolled film and the other of the first and second resin films retaining the bonded first and second orally administrable edible agent layers, and pressurizing the resin films at back surfaces by the pair of press rolls so as to bond the first, second and third orally administrable edible agent layers together such that ingredients of each of the orally administrable edible agent layers do not permeate any other of the orally administrable edible agent layers, wherein the third orally administrable edible agent layer includes the same ingredients or different ingredients as that of the bonded first and second orally administrable edible agent layers; and delaminating only one of the resin films sandwiching the bonded first, second and third orally administrable edible agent layers by conveying the resin films sandwiching the bonded first, second and third orally administrable edible agent layers in the substantially tangential direction at the pressurization zone of the pair of press rolls, and drawing only one of the resin films sandwiching the bonded first, second and third orally administrable edible agent layers in a direction different from the conveying direction along the peripheral surface of the delamination roll disposed in the conveying direction while continuously conveying the other of the resin films retaining the bonded first, second and third orally administrable edible agent layers in the conveying direction.

25. The method for producing an orally administrable edible agent of laminate film form according to claim 24, wherein the one resin film to be delaminated in said delaminating of only one of the resin films sandwiching the bonded first, second and third orally administrable edible agent layers is previously subjected to release treatment on both a front surface to be provided with an orally administrable edible agent layer and an opposite back surface, and the other of the resin films on which the bonded first, second and third orally administrable edible agent layers are to be retained in said delaminating of only one of the resin films sandwiching the bonded first, second and third orally administrable edible agent layers is previously subjected to release treatment at least on a back surface which is not to be provided with an orally administrable edible agent layer.

26. The method for producing an orally administrable edible agent of laminate film form according to claim 24, wherein the one resin film to be delaminated in said delaminating of only one of the first and second resin films is previously subjected to release treatment on both a front surface to be provided with an orally administrable edible agent layer and an opposite back surface, and the other of the resin films on which the bonded first and second orally administrable edible agent layers are to be retained in said delaminating of only one of the first and second resin films is previously subjected to release treatment at least on a back surface which is not to be provided with an orally administrable edible agent layer.

27. The method for producing an orally administrable edible agent of laminate film form according to claim 24, wherein said pressurizing of the resin films in said joining together of the first and second rolled films and in said joining together of the third rolled film and the roll having the bonded first and second orally administrable edible agent layers comprises pressurizing the resin films at a pressure of 0.05 to 1.5 MPa.

28. The method for producing an orally administrable edible agent of laminate film form according to claim 24, wherein a temperature of the orally administrable edible agent layers is 50° C. to 180° C. during said joining together of the first and second rolled films and during said joining together of the third rolled film and the roll having the bonded first and second orally administrable edible agent layers.

29. The method for producing an orally administrable edible agent of laminate film form according to claim 24, wherein a thickness of each of the bonded first, second and third orally administrable edible agent layers is 1 to 300 μm.

30. The method for producing an orally administrable edible agent of laminate film form according to claim 24, wherein the bonded first, second and third orally administrable edible agent layers are self-supporting laminated films.

31. A pressure bonding apparatus for producing an orally administrable edible agent of laminate film form, comprising:

a pair of press rolls arranged to draw two resin films, each of said resin films being provided with an orally administrable edible agent layer having a predetermined thickness on a surface thereof, such that orally administrable edible agent layer surfaces face each other and said orally administrable edible agent layers are sandwiched between said resin films, said pair of press rolls being further arranged to pressurize said resin films at back surfaces thereof so as to bond said orally administrable edible agent layers together such that ingredients of each of said orally administrable edible agent layers do not permeate the other of said orally administrable edible agent layers;

a delamination roll having a diameter of 6 cm or less disposed at a position forward of said pair of press rolls in a conveying direction of said pair of press rolls and in a substantially tangential direction at a pressurization zone of said pair of press rolls;

a winding shaft arranged to draw and delaminate only one of said two resin films sandwiching said orally administrable edible agent layers conveyed from said pair of press rolls to said delamination roll in a direction different from the conveying direction from said pair of press rolls to said delamination roll, along a peripheral surface of said delamination roll; and a conveyance mechanism arranged to convey the other of said two resin films, which retains said orally administrable edible agent layers, in the conveying direction from said pair of press rolls to said delamination roll.

32. The pressure bonding apparatus for producing an orally administrable edible agent of laminate film form according to claim 31, wherein said delamination roll is rotatably disposed so as to rotate with movement of said one resin film.

33. The pressure bonding apparatus for producing an orally administrable edible agent of laminate film form according to claim 31, wherein said winding shaft is disposed in a position so as to draw said one resin film at an angle of 45° or more relative to the conveying direction of said other of said two resin films with said delamination roll as a starting point.

34. The pressure bonding apparatus for producing an orally administrable edible agent of laminate film form according to claim 31, further comprising:
    a pair of unwinding rolls arranged to respectively feed said two resin films to said pair of press rolls; and
    a winding roll arranged to wind up said other of said two resin films, which retains said orally administrable edible agent layers,
    wherein said unwinding roll and said winding roll have substantially the same dimension and structure and are interchangeable.

35. The pressure bonding apparatus for producing an orally administrable edible agent of laminate film form according to claim 31, further comprising:
    a slitter arranged to cut said other of said two resin films, which retains said orally administrable edible agent layers, into narrow strips in parallel with the conveying direction; and
    a plurality of winding reels arranged to wind up the narrow strips, respectively, each of said winding reels including a winding shaft portion and a flange portion,
    wherein said plurality of winding reels are arranged so that said winding shaft portions are staggered in backward and forward directions without gaps, and so that said flange portions are aligned in the backward and forward directions.

36. The pressure bonding apparatus for producing an orally administrable edible agent of laminate film form according to claim 35, further comprising:
    a shaft arranged to support said plurality of winding reels; and
    frames arranged so as to support both ends of said shaft, respectively, wherein one end of said shaft can be supported so as to be cantilevered by one of said frames, and the other of said frames can be brought down and stood up.

37. The pressure bonding apparatus for producing an orally administrable edible agent of laminate film form according to claim 35, further comprising:
    a shaft arranged to rotatably support each of said winding reels; and
    a spring disposed at one end of said shaft and biased toward an opposite end of said shaft, said spring being arranged such that side walls of each winding reel are pressed by said spring, and such that a biasing force of said spring causes rotation of the shaft to be transmitted to said winding reels.

38. The pressure bonding apparatus for producing an orally administrable edible agent of laminate film form according to claim 31, further comprising:
    a slitter arranged to cut said other of said two resin films, which retains said orally administrable edible agent layers, into narrow strips in parallel with the conveying direction, said slitter being switchable between an ON state in which said slitter cuts said other of said two resin films into narrow strips in parallel with the conveying direction, and an OFF state in which said other resin film passes through said slitter without being cut;
    a shaft arranged to support a plurality of winding reels, said winding reels being arranged to wind up said narrow strips, respectively, from said slitter in the ON state; and
    a winding roll arranged to wind up said other resin film conveyed by said conveyance mechanism through said slitter in the OFF state,
    wherein said winding roll and said shaft that supports said plurality of winding reels are interchangeable.

* * * * *